(12) United States Patent
Badik et al.

(10) Patent No.: US 12,226,162 B2
(45) Date of Patent: Feb. 18, 2025

(54) SMART EYE MASK

(71) Applicant: KURE, LLC, Newark, DE (US)

(72) Inventors: Yale Badik, Madison, CT (US); Deanna Felker, West Hills, CA (US)

(73) Assignee: KURE, LLC, Newark, NJ (US)

( * ) Notice: Subject to any disclaimer, the term of this patent is extended or adjusted under 35 U.S.C. 154(b) by 0 days.

(21) Appl. No.: 17/739,588

(22) Filed: May 9, 2022

(65) Prior Publication Data

US 2023/0355090 A1     Nov. 9, 2023

(51) Int. Cl.
| | | |
|---|---|---|
| A61B 3/113 | (2006.01) | |
| A61B 5/00 | (2006.01) | |
| A61B 5/107 | (2006.01) | |
| A61F 13/12 | (2006.01) | |
| G06F 3/01 | (2006.01) | |

(52) U.S. Cl.
CPC ............ *A61B 3/113* (2013.01); *A61B 5/1075* (2013.01); *A61B 5/4058* (2013.01); *A61F 13/124* (2013.01); *G06F 3/013* (2013.01)

(58) Field of Classification Search
CPC ..... A61B 3/113; A61B 5/1075; A61B 5/4058; A61F 13/124
See application file for complete search history.

(56) References Cited

U.S. PATENT DOCUMENTS

| | | |
|---|---|---|
| 6,193,740 B1 | 2/2001 | Rodriguez |
| 7,707,655 B2 | 5/2010 | Braunecker et al. |
| RE42,471 E | 6/2011 | Torch |
| 8,082,452 B2 | 12/2011 | Jajodia |
| 8,566,269 B2 | 10/2013 | Jajodia et al. |
| 8,636,786 B2 | 1/2014 | Biser |
| 8,870,740 B2 | 10/2014 | Clegg et al. |
| 9,203,861 B2 | 12/2015 | Albanese et al. |
| 9,436,822 B2 | 9/2016 | Ghosh et al. |
| 9,846,588 B2 | 12/2017 | Ghosh et al. |
| 10,349,177 B2 | 7/2019 | Hanson |
| 10,905,846 B2 | 2/2021 | Weber et al. |
| 10,956,184 B2 | 3/2021 | Ghosh et al. |
| 10,974,020 B2 | 4/2021 | Rabin et al. |
| 11,073,908 B2 | 7/2021 | Gustafsson et al. |
| 2003/0014096 A1* | 1/2003 | Burkhart .................. A61F 9/04 607/109 |
| 2004/0059212 A1* | 3/2004 | Abreu ................ A61B 5/14553 374/E13.002 |
| 2005/0070977 A1 | 3/2005 | Molina |
| 2009/0264789 A1* | 10/2009 | Molnar .............. A61N 1/36135 600/595 |
| 2010/0054481 A1 | 3/2010 | Jajodia et al. |
| 2010/0058456 A1 | 3/2010 | Jajodia et al. |

(Continued)

*Primary Examiner* — Oommen Jacob
(74) *Attorney, Agent, or Firm* — Raj S. Dave; Dave Law Group LLC

(57) ABSTRACT

Embodiments relate to an object comprising a mask comprising a first portion to cover an eye of a person, the first portion comprising: a first layer and a second layer adjacent to the first layer; an eye pocket; an attachable device; and a bio-monitoring system; wherein the first layer and the second layer form a pouch; and wherein the bio-monitoring system monitors a physiological state of the person, a method of providing a therapy to a person using the object and a method for estimating an effect of the therapy through movement of eyes using the object.

16 Claims, 21 Drawing Sheets

(56) References Cited

U.S. PATENT DOCUMENTS

| | | | |
|---|---|---|---|
| 2015/0206366 A1* | 7/2015 | DiVincent | G07C 9/37 |
| | | | 340/5.52 |
| 2016/0314468 A1* | 10/2016 | Smith | G07F 7/1041 |
| 2017/0059865 A1* | 3/2017 | Komaki | G09B 5/02 |
| 2017/0252210 A1 | 9/2017 | Bruder | |
| 2017/0266035 A1 | 9/2017 | Kuo | |
| 2018/0279935 A1* | 10/2018 | Whang | A61B 5/163 |
| 2020/0026087 A1 | 1/2020 | Cai et al. | |
| 2020/0147038 A1* | 5/2020 | Russ | A61K 31/65 |
| 2020/0179349 A1* | 6/2020 | Yun | A61K 31/437 |
| 2020/0215296 A1* | 7/2020 | Rabin | G05B 19/416 |
| 2020/0261689 A1 | 8/2020 | Harrison et al. | |
| 2020/0410644 A1 | 12/2020 | Connor | |
| 2021/0015659 A1 | 1/2021 | Lau et al. | |
| 2021/0204852 A1 | 7/2021 | Samadani | |
| 2022/0319669 A1* | 10/2022 | Greenbaum | G16H 20/70 |
| 2023/0031613 A1* | 2/2023 | Fleury | A61B 5/6803 |

* cited by examiner

SMART EYE MASK

FIELD OF THE INVENTION

This invention relates generally to the field of masks. More particularly, the present invention relates to a wireless stereo eye mask that provides therapeutic stimuli to a person.

RELATED APPLICATIONS

The present invention is related to U.S. patent application Ser. No. 17/739,463; filed May 9, 2022 entitled TREATMENT CHAIR; application Ser. No. 17/739,673; filed May 9, 2022 entitled INFUSION AND MONITORING SYSTEM; application Ser. No. 17/739,756; filed May 9, 2022 entitled SMART STORAGE SYSTEM application Ser. No. 17/739,835; filed May 9, 2022 entitled SMART DISPENSING SYSTEM which are being concurrently filed. All U.S. Patent Applications referred above are incorporated, for the purposes of written description, herein by reference in their entirety.

BACKGROUND

"Sympathetic and parasympathetic activity make up a complex, dynamic system that is continuously adjusting to changing conditions in the body and in the external environment. The ANS strives to optimize activity in each branch and to balance the two branches in real time, depending on both internal and external conditions, thereby maintaining homeostasis. In certain diseases and conditions, the balance between sympathetic and parasympathetic system activity is implicated either causally or in attempted remediation. Accordingly, ways for affecting a subject's health or condition by stimulating and refining the function of the sympathetic and/or parasympathetic branches of the ANS, both acutely and progressively over time, are desired" [Source: Systems and methods of mitigating negative effects of therapies with transcutaneous vibration; Lowell and Fantauzzi; issued as U.S. Ser. No. 10/974,020B2 on 13 Apr. 2021]

"A wireless stereo sleep mask is an apparatus that is used to block light from entering a user's eyes, while simultaneously providing the user a way to wirelessly interact with a smartphone or other similar devices. The apparatus includes an eye cover, an elastic strap, a first speaker, a second speaker, a control unit, and a wireless transceiver. The eye cover prevents light from disturbing the user." [Source: Wireless stereo sleep mask; Cherie Hanson; issued as U.S. Ser. No. 10/349,177B2 on 9 Jul. 2019]

"A therapeutic mask for treatment of the eyes, including an eye coverage portion for application to the eye, a receiver in the eye coverage portion positioned to align with the eye, and at least one pod for detachably securing within the receiver. The pod includes material for delivering thermal, moisture and/or medication therapy and treatment to the eye." [Source: Therapeutic eye mask system; Mark H. Bruder; published as US20170252210A1 on 7 Sep. 2017]

"A system in which a wearable device detects an electroencephalographic (EEG) response from a user during sleep-related activity, e.g. trying to fall asleep, being asleep or waking up, and outputs an audio signal that is tailored, based on the EEG response, to enhance the user's sleep experience. In particular, an audio, thermal and/or olfactory signal may be used to facilitate any one or more of (i) a smooth path into rapid eye movement (REM) sleep, (ii) a reduced potential for sleep being disturbed, and (iii) exit from sleep at an optimum time." [Source: Sleep enhancement system and wearable device for use therewith; Harrison and Morgan; published as US20200261689A1 on 20 Aug. 2020]

"[T]he sensor was capable to detect various movements of eyelid and eyeballs from the most-comfortably-wearable temple area. This noninvasive, nontoxic, and easily-wearable eye movement sensor can detect eye blink frequency, blink duration, and percent of eye closure to function as an objective indicator of eye strain, fatigue, and drowsiness. The sensor can also measure lateral movements of eyeballs, which are distinguished from the eye blink . . . " [Source: Kim et. al., Highly-Sensitive Skin-Attachable Eye-Movement Sensor Using Flexible Nonhazardous Piezoelectric Thin Film. Adv. Funct. Mater. 2021, 31, 2008242.]

Considering the knowledge of persons skilled in the art, there is a long-felt need to address the shortcomings in the prior art and provide an object that provides a therapeutic stimulus to a person and monitors an effect of the therapy simultaneously. It would be advantageous to have a device that considers at least some of the issues discussed above, as well as possibly other issues.

SUMMARY

The present disclosure describes one or more aspects of providing an object that gives a therapeutic stimulus to a person while also monitoring an effect of the therapy.

In an aspect, an object is described herein. The object comprises a mask comprising a first portion to cover an eye of a person, the first portion comprising: a first layer and a second layer adjacent to the first layer; an eye pocket; an attachable device; and a bio-monitoring system; wherein the first layer and the second layer form a pouch; and wherein the bio-monitoring system monitors a physiological state of the person.

In an aspect, an object is described herein. The object comprises a mask comprising a first portion to cover an eye of a person, the first portion comprising: a first layer and a second layer adjacent to the first layer; an eye pocket; an attachable device; and a bio-monitoring system; wherein the first layer and the second layer form a pouch; and wherein the bio-monitoring system monitors a physiological state of the person.

In an embodiment, the first layer and the second layer are made from one of a silk fabric, a cotton fabric, a wool fabric, a nylon fabric, a velvet fabric, a polyester fabric, a synthetic fabric, a suitable fabric, and combination thereof.

In another embodiment, the eye pocket is deep molded and concave.

In yet another embodiment, the eye pocket further comprises a 3D contoured cup.

In yet another embodiment, the 3D contoured cup is configured to apply stress-relieving pressure around the eye.

In yet another embodiment, the 3D contoured cup is configured to form a space between the eye and the eye pocket.

In yet another embodiment, the space can hold a pad on and around the eye.

In yet another embodiment, the pad is selected from one of a patch, an eye pillow, and a gel pad.

In yet another embodiment, the pad comprises a nutrient composition.

In yet another embodiment, the pad comprises a hydrating composition.

In yet another embodiment, the pad comprises a heating gel.

In yet another embodiment, the pad comprises a cooling gel.

In yet another embodiment, the bio-monitoring system sends data to a biofeedback control system.

In yet another embodiment, the bio-monitoring system is inbuilt.

In yet another embodiment, the bio-monitoring system is removable.

In yet another embodiment, the attachable device can be selected from a group comprising an audio device, a microphone, an aroma infusion device, a visual display, a heating device, a cooling device, an eye massage device, and a light emitting device.

In yet another embodiment, the attachable device and the bio-monitoring system can be remotely controlled via a computing system.

In yet another embodiment, the bio-monitoring system comprises at least one of an eye blink sensor and an eye movement sensor.

In yet another embodiment, the bio-monitoring system further comprises at least one of a blood pressure measurement sensor, a pulse measurement sensor, an electrolyte levels measurement sensor, an oxygen level measurement sensor, a glucose level measurement sensor, and a body temperature measurement sensor.

In yet another embodiment, the pouch is zipper lined.

In yet another embodiment, a second portion of the mask comprises an adjustable strap.

In yet another embodiment, the adjustable strap is one of a buckle strap, elastic strap, clip-on strap and velcro strap.

In yet another embodiment, the adjustable strap is an elastic strap.

In yet another embodiment, the object is washable and reusable.

In yet another embodiment, the pouch is filled with a fill material.

In yet another embodiment, the fill material comprises an aromatic substance.

In yet another embodiment, the aromatic substance comprises single essential oil or a combination of essential oils.

In yet another embodiment, the fill material comprises a thermally conductive material.

In yet another embodiment, the thermally conductive material comprises at least one of an organic material, a gel bead, and an exothermic material composition.

In yet another embodiment, the fill material comprises a plurality of electro-magnets.

In yet another embodiment, the fill material is filled and removed manually.

In yet another embodiment, the object comprises a control unit.

In yet another embodiment, the control unit comprises an input module, a processor, a communication module, a database, a user interface, a universal serial bus, a controller, a display, and a power module.

In yet another embodiment, the power module further comprises one or more of a rechargeable battery, a non-rechargeable battery, a solar cell, a chemical reaction power generator, a power input port that connects to an external power line, or any other device configured to provide power to components of the object.

In yet another embodiment, the power module is arranged and disposed to provide wireless charging with an induction charger.

In yet another embodiment, the object can be used as an attachment in an article of furniture.

In yet another embodiment, the object can communicate data to a server via the communication module.

In yet another embodiment, the control unit comprises a cyber security module.

In yet another embodiment, the cyber security module further comprises an information security management module providing isolation between the system and the server.

In yet another embodiment, the information security management module is operable to: receive data from at least one of the user interface, the bio-monitoring system, the attachable device, and the database; exchange a security key at a start of the communication between the communication module and the server; receive the security key from the server; authenticate an identity of the server by verifying the security key; analyze the security key for a potential cyber security threat; negotiate an encryption key between the communication module and the server; encrypt the data; and transmit the encrypted data to the server when no cyber security threat is detected.

In yet another embodiment, the information security management module is operable to: exchange a security key at a start of the communication between the communication module and the server; receive the security key from the server; authenticate an identity of the server by verifying the security key; analyze the security key for a potential cyber security threat; negotiate an encryption key between the system and the server; receive encrypted data; decrypt the encrypted data; perform an integrity check of the decrypted data; and transmit the decrypted data to at least one of the user interface, the bio-monitoring system, the attachable device, and the database through the communication module when no cyber security threat is detected.

In yet another embodiment, the information security management module is configured to raise an alarm when a cyber security threat is detected.

In yet another embodiment, the information security management module is configured to discard the encrypted data received if the integrity check of the encrypted data fails.

In yet another embodiment, the information security management module is configured to check the integrity of the encrypted data by checking accuracy, consistency, and any possible data loss during the communication through the communication module.

In yet another embodiment, the information security management modules is configured to perform asynchronous authentication and validation of the communication between the communication module and the server.

In yet another embodiment, wherein a perimeter network provides an extra layer of protection.

In yet another embodiment, the perimeter network protects the system from a cyber security threat by using a plurality of firewalls.

In an aspect, a method is described herein. The method comprises steps of: providing a therapy to a person using an object; monitoring a physiological state of the person using the object; and estimating an effect of the therapy using a bio-monitoring system that monitors a change in the physiological state of the person; and modifying the therapy based on the change in the physiological state; wherein the object comprises a mask comprising a first layer and a second layer adjacent to the first layer; an eye pocket; an attachable device; and a bio-monitoring system; wherein the first layer and the second layer form a pouch; and wherein the bio-monitoring system monitors a physiological state of the person.

In an embodiment, the therapy comprises one or more of a drug therapy, a sound therapy, an aromatherapy, an acupressure therapy, a massage therapy, a temperature therapy, a magnetic therapy, and a visual based stress relief therapy.

In another embodiment, the therapy comprises a psychedelic therapy.

In yet another embodiment, the attachable device can be selected from a group comprising an audio device, a microphone, an aroma infusion device, a visual display, a heating device, a cooling device, an eye massage device, and a light emitting device.

In yet another embodiment, the bio-monitoring system comprises at least one of an eye blink sensor, an eye movement sensor, a web camera, a blood pressure measurement sensor, a pulse measurement sensor, an electrolyte levels measurement sensor, an oxygen level measurement sensor, a glucose level measurement sensor, and a body temperature measurement sensor.

In yet another embodiment, the bio-monitoring system sends data to a biofeedback control system that controls a delivery of a drug to the person.

In yet another embodiment, the method further comprises steps of: storing data from the bio-monitoring system and the attachable device to a database; securing data access using a cyber security module; accessing the data from the database from a remote location via the cyber security module through authentication; and sending an instruction to the person or a caregiver via a communication module In an aspect, a method is described herein. The method comprises: providing a therapy; and estimating an effect of the therapy through movement of eyes using an object; wherein the object comprises a mask that comprises a bio-monitoring system wherein the bio-monitoring system monitors a physiological state of a person.

In an embodiment, the bio-monitoring system comprises an eye blink sensor and an eye movement sensor.

In another embodiment, wherein the bio-monitoring system comprises a web camera for pupil size measurements.

In yet another embodiment, the bio-monitoring system further comprises a blood pressure measurement sensor, a pulse measurement sensor, an electrolyte levels measurement sensor, an oxygen level measurement sensor, a glucose level measurement sensor, and a body temperature measurement sensor.

In yet another embodiment, the bio-monitoring system transmits a signal to a remote receiver.

In yet another embodiment, the therapy is a psychedelic therapy.

BRIEF DESCRIPTION OF THE FIGURES

In the present disclosure, reference is made to the accompanying drawings, which form a part hereof. In the drawings, similar symbols typically identify similar components, unless context dictates otherwise. Various embodiments described in the detailed description, and drawings, are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein. The embodiments are illustrated by way of example and not limitation in the figures of the accompanying drawings, in which like references indicate similar elements and in which.

DETAILED DESCRIPTION

Definitions and General Techniques

Figure 1A:
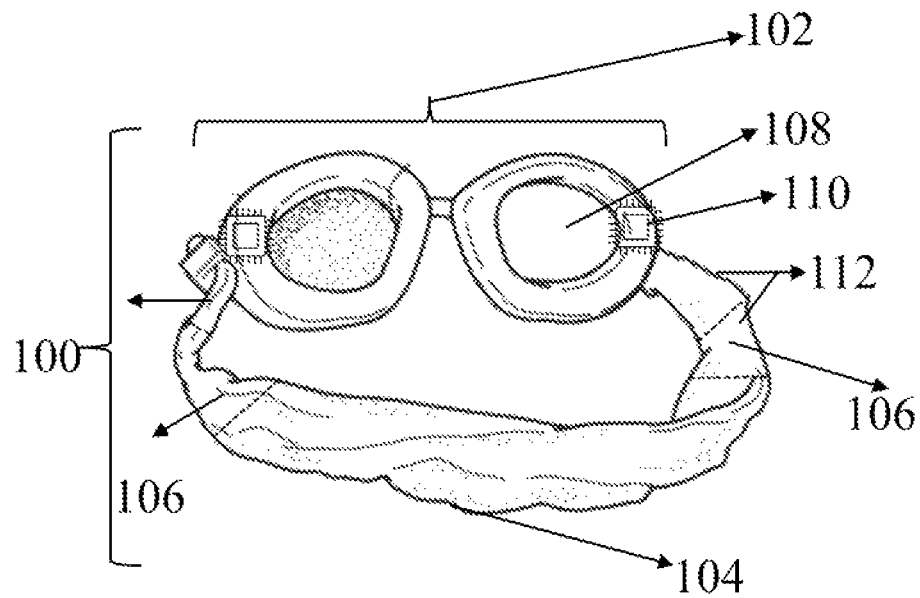
FIG. 1A provides a perspective view of an object, in one or more embodiments.

For simplicity and clarity of illustration, the drawing figures illustrate the general manner of construction. Descriptions and details of well-known features and techniques may be omitted to avoid unnecessarily obscuring the present disclosure. The dimensions of some of the elements in the figures may be exaggerated relative to other elements to help improve understanding of embodiments of the present disclosure. The same reference numeral in different figures denotes the same elements.

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only and is not intended to be limiting. Unless defined otherwise, all technical and scientific terms used herein have the same meaning as commonly understood by one with ordinary skill in the art to which this disclosure belongs.

The articles "a" and "an" are used herein to refer to one or to more than one (i.e., to at least one) of the grammatical object of the article. By way of example, "an element" means one element or more than one element.

The terms "first", "second", "third", and the like in the description and in the claims, if any, are used for distinguishing between similar elements and not necessarily for describing a particular sequence or chronological order. It is to be understood that the terms so used are interchangeable under appropriate circumstances such that the embodiments described herein are, for example, capable of operation in sequences other than those illustrated or otherwise described herein. Furthermore, the terms "include", "have", and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left", "right", "front", "back", "top", "bottom", "over", "under" and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element act, or instruction used herein should be construed as critical or essential unless explicitly described as such. Furthermore, as used herein, the term "set" is intended to include items (e.g., related items, unrelated items, a combination of related items and unrelated items, etc.), and may be used interchangeably with "one or more". Where only one item is intended, the term "one" or similar language is used. Also, as used herein, the terms "has", "have", "having", or the like are intended to be open-ended terms. Further, the phrase "based on" is intended to mean "based, at least in part, on" unless explicitly stated otherwise.

It should be understood that the terms "system," "device," "unit," and/or "module" are used in this disclosure to refer to a different component, component, portion, or component of the different levels of the order. However, if other expressions may achieve the same purpose, these terms may be replaced by other expressions.

The terms "couple", "coupled", "couples", "coupling", and the like should be broadly understood and refer to as connecting two or more elements mechanically, electrically, and/or otherwise. Two or more electrical elements may be electrically coupled together, but not be mechanically or otherwise coupled together. Coupling may be for any length of time, e.g., permanent, or semi-permanent or only for an instant. "Electrical coupling" includes electrical coupling of all types. The absence of the word "removably", "removable", and the like near the word "coupled", and the like does not mean that the coupling, etc. in question is or is not removable.

As defined herein, two or more elements or modules are "integral" or "integrated" if they operate functionally together. As defined herein, two or more elements are "non-integral" if each element can operate functionally independently.

As defined herein, "real-time" can, in some embodiments, be defined with respect to operations carried out as soon as practically possible upon occurrence of a triggering event. A triggering event can include receipt of data necessary to execute a task or to otherwise process information. Due to delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining)

and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All variations which come within the meaning and range of equivalency of the claims are to be embraced within their scope.

As defined herein, "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific, and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Even though particular combinations of features are disclosed in the specification, these combinations are not intended to limit the disclosure of possible implementations.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

An initial overview of technology embodiments is provided below, and specific technology embodiments are then described in further detail. This initial summary is intended to aid readers in understanding the technology more quickly but is not intended to identify key or essential technological features, nor is it intended to limit the scope of the claimed subject matter.

The embodiments herein and the various features and advantageous details thereof are explained more fully with reference to the non-limiting embodiments that are illustrated in the accompanying drawings and detailed in the following description.

In order to fully understand the scope of the invention, the following terms used herein are hereby defined.

As referred herein, "mask" is a covering or blindfold tied to one's head to cover the eyes to block the wearer's sight.

As referred herein, the term "patient" or "subject" or "user" or "person" refers to a person receiving or registered to receive medical treatment. A patient is also referred to as a user as he receives treatment using the therapy system.

As referred herein, "eye pockets" are the countered spaces in the mask provided near the eyes to form an eye cavity that allows easy eye movements and easy eye blinking without hitting the eyelashes to the mask.

As referred herein, "attachable device" is a device capable of connecting with at least one attached device. The attachable device and the attached device are electrically interconnected. The connection can be a wired connection or wireless connection. The attachable device can support signal capturing, signal processing, signal transmission, signal display, signal storage and/or power provision. The signals can be, for example, analog or digital signals. The attachable device can, for example, be used to provide audio output and/or audio pick-up.

As referred herein, "computing device" is a functional unit that can perform substantial computations, including numerous arithmetic operations and logic operations without human intervention. A computing device can consist of a standalone unit or several interconnected units. It can also be a device that provides a specific set of functions, such as a phone or a personal organizer, or more general functions such as a laptop or desktop computer.

As referred herein, "bio-monitoring system" is a system comprising devices and programs connected to electrical sensors that help in receiving information about physiological and mental state of a wearer's body. The information comprises one or more of electromyograph (EMG), thermal biofeedback, neurofeedback/electroencephalograph (EEG), electrodermograph (EDG), heat flux, pneumograph, capnometer data, hemoencephalography, and photoplethysmograph (PPG).

In an embodiment, the bio-monitoring system can be a portable and wearable solution.

As referred herein, "eye monitoring system" is a device that tracks an eye activity. The term Eye activity as used herein refers to a point of gaze (where one is looking), a motion of an eye relative to the head, eye position, size of pupil, pupil dilation or constriction, blinking patterns, visual attention etc.

As referred herein, "sensor" is a device, module, machine, or subsystem whose purpose is to detect physiological or biometric changes and send the information to other electronics, frequently a computer processor. The sensor is used with other electronics, and it enables recording, presentation or response to such detection or measurement using a processor and optionally memory. A sensor and processor can take one form of information and convert such information into another form, typically having more usefulness than the original form. For example, a sensor may collect raw physiological or environmental data from various sensors and process this data into a meaningful assessment, such as pulse rate, blood pressure, or air quality using a processor. A "sensor" herein can also collect or harvest acoustical data for biometric analysis (by a processor) or for digital or analog voice communications. A "sensor" can include any one or more of a physiological sensor (e.g., blood pressure, heart beat, etc.), a biometric sensor (e.g., a heart signature, a fingerprint, etc.), an environmental sensor (e.g., temperature, particles, chemistry, etc.), a neurological sensor (e.g., brainwaves, EEG, etc.), or an acoustic sensor (e.g., sound pressure level, voice recognition, sound recognition, etc.) among others. A variety of microprocessors or other processors may be used herein. Although a single processor or sensor may be represented in the figures, it should be understood that the various processing and sensing functions can be performed by a number of processors and sensors operating cooperatively or a single processor and sensor arrangement that includes transceivers and numerous other functions as further described herein.

As referred herein, "pouch" is an enclosure in the mask where a plurality of devices or material can be put. The pouches are spill proof and zipper-lined to adjust a filling to fit pressure preferences.

As referred herein, "physiological state" is a condition or state of the body, bodily functions, mental state, and emotional state of a living being. Examples include but not limited to asphyxia, consciousness, alertness, acapnia, hypercapnia, hypothermia, hyperthermia, upset, cryptobiosis, good health, myasthenia, atherosclerosis, myocardial infarction, angina pectoris, arrhythmias (irregular heartbeat), chronic heart failure, blood pressure, glucose or blood sugar, temperature, drowsiness, hallucinations, slow breathing, dry mouth, anxiety, vomiting, confusion, drowsiness, slurred speech, rambling speech, lack of coordination, mood changes, involuntary eye movement, dizziness, alertness, restlessness, dilated pupils, nasal congestion, behavior changes, chills, sweating, loss of memory, teeth clenching, coordination problems, impulsive behavior, pain sensitivity, tremors, rashes, euphoria, sense of pain, etc. Some signs may be directly measured, for example, heart rate and some may be indirectly measured, for example, measuring brain activity to analyze the state of consciousness. In the embodiments herein, the term "physiological" is intended to be used broadly, covering both physical and psychological characteristics of or from the body of an organism.

As referred herein, "deep molded" to create a vertical distance from the top of the pocket to the rim of the cup.

As referred herein, "3D contoured cup" is the 3-dimensional eye wires or rims contoured around the eye socket such that they apply stress-relieving pressure around the eyes instead of on them.

As referred herein, "stress relieving pressure" is a pressure that is used to stimulate specific points on the body along a pressure point. The meaning of pressure point is an area on the body sensitive to pressure.

As referred herein, "eye patch" or "patch" is a soft medical sticking plaster that can be attached to and detached from the skin. These blind patches are designed to be in an oval shape and to be attached so that the narrower end faces the nose.

As referred herein, "eye pillows" also known as "dream pillows" or "comfort pillows" are small, double-sided pillows designed to comfortably cushion the eyes. These pillows are typically used to shield the eyes from light and to apply a gentle relaxing weight over and around the eyes. They are to ease nightmares and to disguise the scent of illness. In an embodiment the eye pillows can be fragrant, heated, or frozen.

As referred herein, "gel pad" is a therapeutic pack comprising a gelatinous material enclosed in an enclosure.

As referred herein, "bio-feedback control system", is a system that controls or improves a treatment plan by making subtle changes, based on the information provided by the bio-monitoring system, to improve a health condition, a physical performance, or benefits of a therapy.

As referred herein, "inbuilt" or "built-in" means forming an integral part of a structure or object.

As referred herein, "audio device" or "sound emitting device" is an output device capable of generating a frequency corresponding to a normally audible sound wave.

As referred herein, "aroma infusion device" is a device that can diffuse aroma into the environment. The aroma infusion device can be selected from an electric aroma lamp diffuser, an oil lamp, air humidifier essential oil diffuser aroma lamp or the like.

As referred herein, "visual display" is a device capable of generating an image or video on a device. The device may comprise a terminal in which a cathode ray tube, liquid-crystal, or plasma display device is used for the visual presentation of data.

As referred herein, "light emitting device" is a device that emits light when an electric current passes through it. In an embodiment, the light therapy device is programmed to emit light based on an input wavelength, of an input color, for an input time. The light emitting device is height and direction adjustable.

As referred herein, "aromatic substances" are organic or chemically synthesized aromatic materials, including essential oils, and other aroma compounds, with claims for improving psychological or physical well-being.

As referred herein, "electro-magnets" is a type of magnet in which the magnetic field is produced by an electric current. Electromagnets usually consist of wire wound into a coil. A current through the wire creates a magnetic field which is concentrated in the hole, denoting the center of the coil. The magnetic field disappears when the current is turned off. The wire turns are often wound around a magnetic core made from a ferromagnetic or ferrimagnetic material such as iron; the magnetic core concentrates the magnetic flux and makes a more powerful magnet.

As referred herein, "vital monitoring system" provides standard data on body temperature, pulse rate, respirations, and blood pressure. It can also provide data on ECG, pulse oximetry ($SPO_2$), end tidal carbon dioxide ($EtCo_2$), cardiac output, and agent analysis.

As referred herein, "electrocardiography" is the process of producing an electrocardiogram (ECG or EKG), a recording of the heart's electrical activity.

As referred herein, "rapid eye movement sleep" (REM sleep or REMS) is a unique phase of sleep in mammals and birds, characterized by random rapid movement of the eyes, accompanied by low muscle tone throughout the body, and the propensity of the sleeper to dream vividly.

As referred herein, "control unit" is an embedded system in an object that controls one or more of the electrical systems, computing systems, electronic systems, or subsystems. In an embodiment the control unit can interact with an external control unit.

As used herein, a "database" is a collection of information that is organized so that it can be easily accessed, managed, and updated. Computer databases typically contain aggregations of data records or files.

The term "communication module" is a module that facilitates communication, that is, it enables transmission and receiving of data from the input and output interfaces to the processor. It also enables communication between the peripheral devices connected with the processor like display, camera, remote servers, and databases. A communication module may be a wired connection between the components or a wireless communication module.

As referred herein, "user interface" is the portion of a firmware system that processes commands entered by a human.

As referred herein, "controller" is a component of a control unit that functions as the system controller. A controller typically sends program messages to and receives response messages from devices. A functional unit in a computer system that controls one or more units of the peripheral equipment. Synonym: peripheral control unit. See also: input-output controller; dual channel controller. In robotics, a processor that takes as input desired and measured position, velocity or other pertinent variables and whose output is a drive signal to a controlling motor or activator. A device through which one can introduce commands to a control system.

As referred herein, "power module" is a module that provides power to the device and the components of the device.

As referred herein, "induction charger" is a device that uses electromagnetic waves to transfer energy and charge devices wirelessly.

As referred herein, "server" is a computer or system that provides resources, data, services, or programs to other computers, known as clients, over a network. In theory, whenever computers share resources with client machines, they are considered servers. There may be Physical Servers and Virtual Servers, that is the server may be a local server or a remote server.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers—say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that an authorized user can only decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damage data, steal data, or disrupt digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attack, data breaches, Denial of Service (DoS) attacks, and other attack vectors.

The term "hash value" used herein can be thought of as fingerprints for files. The contents of a file are processed through a cryptographic algorithm, and a unique numerical value—the hash value—is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application. Data integrity refers to the accuracy and consistency (validity) of data over its lifecycle. Compromised data is of little use to enterprises, not to mention the dangers presented by sensitive data loss.

The term "alarm" as used herein refers to a trigger when a component in a system or system fails or does not perform as expected. System may enter an alarm state when a certain event occurs. An alarm Indication signal is a visual signal to indicate the alarm state. For example, the heart rate is very low, a light emitting diode (LED) may glow red alerting that it is beyond the specified limits, and it turns green when the heart rate is within specified limits. Another example could be, when a cyber security threat is detected, a network administrator may be alerted via sound alarm, a message, a glowing LED, a pop-up window, etc. Alarm indication signal may be reported downstream from a detecting device, to prevent adverse situations or cascading effects.

The term "in communication with" as used herein, refers to any coupling, connection, or interaction using electrical signals to exchange information or data, using any system, hardware, software, protocol, or format, regardless of whether the exchange occurs wirelessly or over a wired connection.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

As used herein, the term "perimeter network" refers to a network closest to a router that is not under the enterprise or organization control. Usually, a perimeter network is the final step a packet takes traversing one of your networks on its way to the internet; and conversely the first network encountered by incoming traffic from the Internet. A network perimeter is a secured boundary between the private and locally managed side of a network, often a company's intranet, and the public facing side of a network, often the Internet. The boundary is defined as a perimeter network.

As used herein, the term "network" may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers. Cloud servers are located in data centers all over the world. By using cloud computing, users and companies don't have to manage physical servers themselves or run software applications on their own machines.

As used herein, the term "system hardening" is a collection of tools, techniques, and best practices to reduce vulnerability in technology applications, systems, infrastructure, firmware, and other areas. The goal of system hardening may be to reduce security risk by eliminating potential attack vectors and condensing the system's attack surface.

As used herein, the term "SHA256" stands for Secure Hash Algorithm 256-bit is a hash function and it is used for cryptographic security. Cryptographic hash algorithms produce irreversible and unique hashes. The larger the number of possible hashes, the smaller the chance that two values will create the same hash.

As referred herein, "psychedelic drug" is psychotomimetic drug or hallucinogen, or any of the so-called mind-expanding drugs that are able to induce states of altered perception and thought, frequently with heightened awareness of sensory input but with diminished control over what is being experienced.

As referred herein, "light therapy" is a way to treat psychological or physiological disorders by exposure to artificial light.

As referred herein, "sound therapy" refers to a range of therapies in which sound is used to treat physical and mental conditions. One of these therapies is music therapy, which can involve a person listening to music for conditions such as stress and muscle tension.

As referred herein, "aromatherapy" is a form of alternative or complementary therapy in which essential oils or other scents are inhaled to achieve therapeutic benefit. It also comprises a range of traditional, alternative, or complementary therapies that use essential oils and other aromatic plant compounds.

As referred herein, "acupressure therapy" is an ancient healing art that uses any blunted objects to press key points called 'acu-points' (energy stored points) on the surface rhythmically on the skin to stimulate the body's natural self-curative abilities. When these points are pressed, they release muscular tension and promote the circulation of blood and the body's life force to aid healing.

As referred herein, "massage therapy" is a type of integrative medicine wherein the soft tissues of the body are manipulated using varying degrees of pressure and movement. Massage involves acting on and manipulating the body with pressure—structured, unstructured, stationary, or moving—tension, motion, or vibration, done manually or with mechanical aids.

As referred herein, "magnetic therapy" is a process of treating a physical, physiological, or psychological problem using a weak static magnetic field. The magnetic field can be produced by a permanent magnet or by an electrically powered device. The magnetic therapy also comprises transcranial magnetic stimulation. It also comprises the medicine practice of electromagnetic therapy, which uses a magnetic field generated by an electrically powered device.

As referred herein, "heat therapy" or "thermotherapy" is the use of heat in therapy, such as for pain relief, rehabilitation purposes, and health. The heat therapy can be done using dry heat and moist heat. Both types of heat therapy should aim for "warm" as the ideal temperature instead of "hot."

As referred herein, "thermally conductive materials" are the substances that are "warm" as the ideal temperature instead of "hot" for a heat therapy. These substances can be solid, liquid, gel, and combination thereof.

As referred herein, "physiologic tunnel" or "tunnel" conveys continuous and integral data on the physiology of the body. An undisturbed signal from within the body is delivered to an external point at the end of the tunnel. A sensor placed on the skin at the end of the tunnel allows optimal signal acquisition without interfering constituents and sources of error.

As referred herein, "clip" is an object used for holding things together preferably by pressure means.

In an aspect, an object is described herein. The object comprises a mask comprising a first portion to cover an eye of a person, the first portion comprising: a first layer and a second layer adjacent to the first layer; an eye pocket; an attachable device; and a bio-monitoring system; wherein the first layer and the second layer form a pouch; and wherein the bio-monitoring system monitors a physiological state of the person.

Figure 1B:
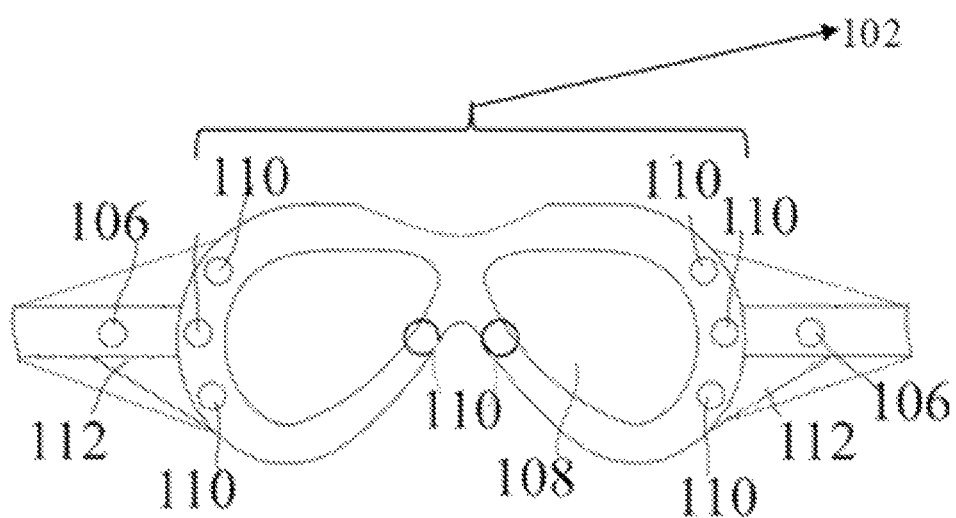
FIG. 1B provides a front view of the object, in one or more embodiments.
Figure 1C:
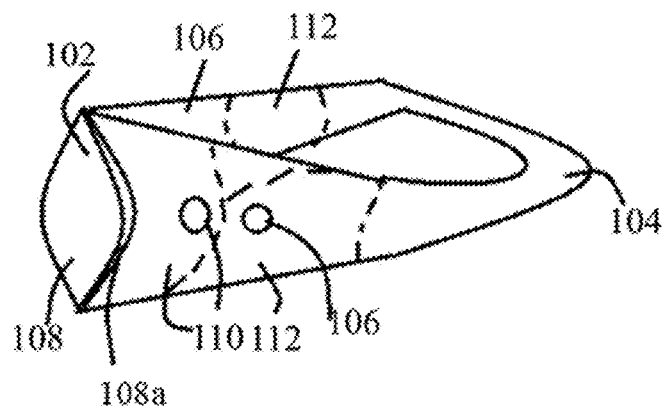
FIG. 1C provides a side view of the object, in one or more embodiments.

FIG. 1A provides an upper view of the object, FIG. 1B provides a front view of the object, and FIG. 1C provides a side view of the object.

In an embodiment, the object comprising the mask 100 has a first portion 102 to cover the eyes and a second portion 104 to secure the object to the head so that it doesn't fall or slip. The first portion 102 has two eye pockets 108, an attachable device 106 and a set of bio-monitoring systems 110. The eye pocket is surrounded by a 3D contoured cup 108a.

In an embodiment, a second portion of the mask comprises an adjustable strap.

In another embodiment, the adjustable strap is one of a buckle strap, elastic strap, clip-on strap or velcro strap.

In another embodiment, the adjustable strap is an elastic strap.

In an embodiment, the first layer and the second layer are made from one of a silk fabric, a cotton fabric, a wool fabric, a nylon fabric, a velvet fabric, a polyester fabric, a synthetic fabric, a suitable fabric, or combination thereof.

In an embodiment, a sponge layer is attached to the first layer and the second layer.

Figure 1D:
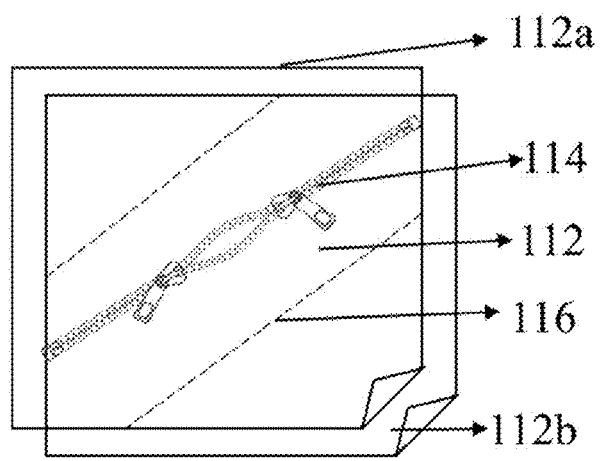
FIG. 1D depicts a pouch in the object, in one or more embodiments.

FIG. 1D depicts a pouch in the object, according to one or more embodiments. The first fabric layer 112a and the second fabric layer 112b are attached intermittently using a suitable means 116 to form a pouch 112 in the object which can be zipper lined 114. The pouches may be soft, flexible, and/or include padding to provide comfort.

In an embodiment, the pouch is filled with a fill material.

In another embodiment, the fill material comprises an aromatic substance.

In yet another embodiment, the aromatic substance comprises single essential oil or a combination of essential oils. The non-limiting examples of essential oil are a pine oil, mandarin oil, bergamot oil, orange oil, lavender oil, clove oil, lemongrass oil, geranium oil, and a combination thereof.

In an embodiment, the fill material comprises a thermally conductive material.

In an embodiment, the thermally conductive material comprises at least one of an organic material, a gel bead, and an exothermic material composition.

In an embodiment, the fill material comprises a plurality of electro-magnets.

In an embodiment, the fill material is filled or removed manually.

In an embodiment, the pouch is zipper lined.

In an embodiment, the eye pocket is deep molded and concave.

In an embodiment, the eye pocket further comprises a 3D contoured cup that supports the eye pocket.

Figure 2A:
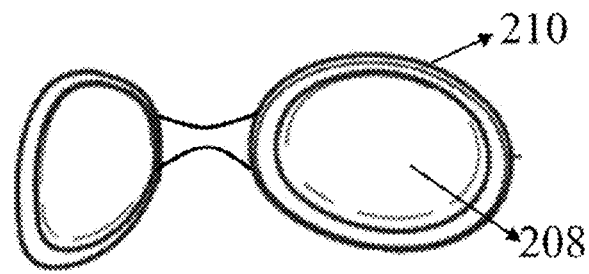
FIG. 2A depicts a 3D contoured cup around an eye pocket of the object, in one or more embodiments.

FIG. 2A depicts a 3D contoured cup around an eye pocket of the object, in one or more embodiments. The first portion of the mask with the eye pocket 208 has a 3D contoured cup 210 around the eye pocket.

Figure 2B:
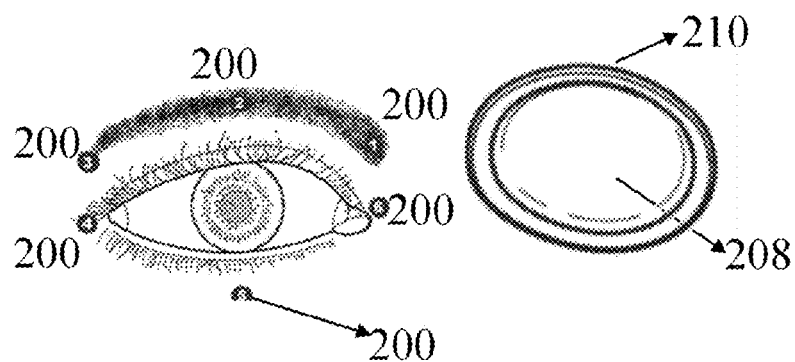
FIG. 2B and FIG. 2C depict application of acupressure on pressure points around an eye via the 3D contoured cup of the object, in one or more embodiments.
Figure 2C:
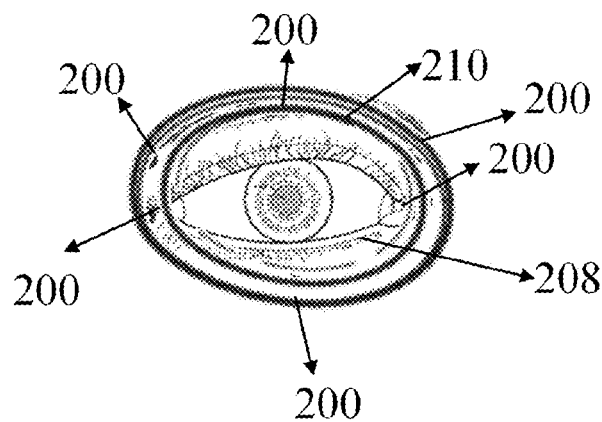

In an embodiment, the 3D contoured cup is configured to apply stress-relieving pressure around the eye. FIG. 2B and FIG. 2C depict application of acupressure on pressure points around an eye via the 3D contoured cup of the object, in one or more embodiments. The pressure points 200 are covered by the 3D contoured cup 210 on the eye and an acupressure is applied simultaneously on the pressure points 200 around the eyes using the object.

In an embodiment, the attachable device can be selected from a group comprising an audio device, a microphone, an aroma infusion device, a visual display, a heating device, a cooling device, an eye massage device, and a light emitting device.

In an embodiment, the attachable device can be attached to the eye pocket by clip-on method or using a velcro.

In an embodiment, the attachable device can be put in the pouches.

In an embodiment, the attachable device is an audio device. The audio device may comprise thick, yet soft, ear covers that provide attenuation of environmental noise, and embedded ear pads with small speakers to deliver audio. The non-limiting examples of audio devices are an ear pod, a micro speaker, or the like.

In an embodiment, the audio delivered by attachable devices comprises one of a healing instrument sound, a programmed meditation audio, a brain stimulating wave frequency, a music, and a nature sound.

In an embodiment, the audio device is equipped with extraneous background noise cancellation capability.

In an embodiment, the attachable device is a visual display. The object may include one or more light emitting diodes or the like in the eye pocket for a visual display. In an example, a plurality of LEDs could be arranged as an array on the eye side surface of at least one of the eye pockets of the mask. The array could display graphics, pictures, or scrolling text.

Figure 3:
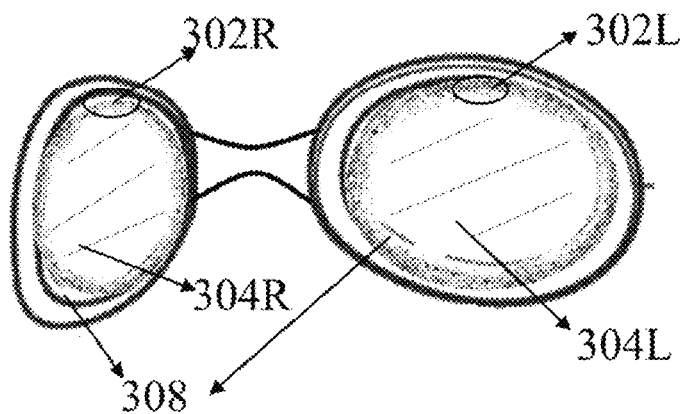
FIG. 3 depicts a mask comprising a visual display, in one or more embodiments.

FIG. 3 depicts a mask comprising a visual display, in one or more embodiments. In an embodiment, the visual display comprises a self-emissive type of electronic display panels comprising micro-pixels. In FIG. 3, the visual display comprises a pair of electronic display panels 302R and 302L that are disposed at a upper edge or upper lateral surface of a prism assembly 304R and 304L. Prism assemblies 304R and 304L resemble and function in the transmission of light from the real-world view as a pair of ophthalmic lenses which lenses may include vision correction. The electronic display panels 302L and 302R may be connected to an external computer or processor through cables coming out of the two ends of the temple elements or wirelessly. The visual display offers high brightness and a high resolution image in a very compact format.

In an embodiment, the attachable device is a light emitting device.

The mask is configured to provide light therapy to a person. The mask may provide a comfortable delivery mechanism for the light therapy and may deliver the light therapy to the person while the person is asleep, in the process of going to sleep, and/or waking from sleep.

Figure 4:
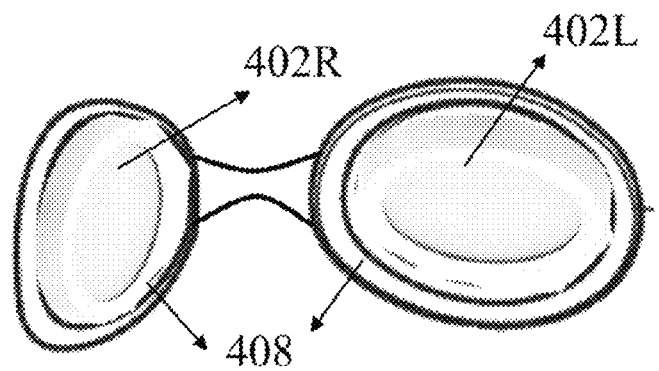
FIG. 4 depicts a mask comprising a light emitting device, in one or more embodiments.

FIG. 4 depicts a mask comprising a light emitting device, in one or more embodiments. The eye pockets 408 of the mask comprise a first light emitting device 402R and/or a second light emitting device 402L.

In an embodiment, the first light emitting device 402R and the second light emitting device 402L comprises one or more radiation sources. The radiation sources are configured to emit radiation and are carried by the eye pocket. One or more radiation diffusers are configured to receive radiation emitted by the one or more radiation sources, and to diffuse the radiation emitted by the one or more radiation sources to form one or more fields of radiation. The one or more radiation diffusers are carried by the eye pocket and are positioned on the eye pocket such that the one or more fields of radiation are directed to the eyes of the person wearing the sleep mask.

In an embodiment, the radiation source comprises side firing light emitting diodes. The backlighting of the light emitting device may be accomplished using other sources and/or configurations. For example, other types of light emitters may be implemented. As another example, in one embodiment, radiation sources are not provided in a side firing configuration, but instead are disposed to emit radiation into a waveguide at back side. The waveguide is configured to receive radiation emitted by radiation sources, and to direct at least some of the received radiation on to the face of the subject on or about the eyes. In this, and other configurations, waveguide still diffuses the light to ensure that the radiation emitted by the light emitting device onto the face of the person has the appropriate uniformity.

In an embodiment, the attachable device is a massage device.

Figure 5:
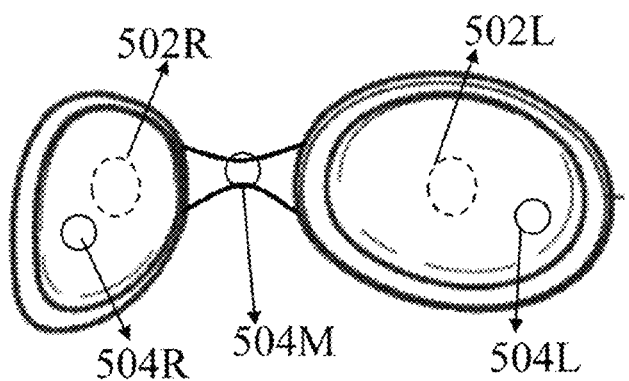
FIG. 5 depicts a mask comprising a massage device, in one or more embodiments.

FIG. 5 depicts a mask comprising a massage device, in one or more embodiments. The massage device may comprise a plurality of vibrators 502R and 502L. The plurality of vibrators 502R and 502L are clipped to the eye pocket 508 and are located just above the eyes of the person when the mask is worn. The distance between the vibrators is between 62 to 66 mm. The vibrators are provided with a vibration frequency of massage motion of between 7000 to 13000 Hz with an output energy of 0.001 watt. The electrical circuit includes a pulse control circuit and a timer. The pulse control circuit operates to activate the vibrators to provide a plurality of selective massage motions, and the timer controls the time period of the massage motions.

In another embodiment, the attachable device may also comprise electric contacts, magnets, fans, heaters, coolers, and/or other devices that can generate stimuli that may be perceived by the person.

In an embodiment, the attachable device can be attached to a control unit via a pulse control circuit for timer-based control or for a regulated operation.

In an embodiment, the bio-monitoring system comprises a plurality of sensors positioned on a physiologic tunnel for measuring physical, chemical, and biological parameters of the body. The measurement of metabolic function, brain function, immunogenic function, physical parameters, physicochemical parameters, and the like includes a variety of support structures with sensors accessing the physiologic tunnels.

The bio-monitoring system is programmed to produce an action according to the measured value of the parameters. In an embodiment, the bio-monitoring system sends data to a biofeedback control system. The biofeedback control system, depending on the present physiological state of the person, controls or improves a treatment plan by making subtle changes to improve a health condition, a physical performance, or benefits of the therapy.

In one embodiment, the bio-monitoring system comprises a first module that contains optical sensors to detect temperature, blood flow and blood oxygen level as well as a speaker to provide wireless communication or hearing aid. The blood flow or velocity information can be used to estimate blood pressure. A second module can contain an array of bioimpedance sensors such as bipolar or tetrapolar bioimpedance probes to sense fluids in the brain. Additional bioimpedance electrodes can be positioned around the 3D contoured cup, eye pockets, as well as pouches or in any spots on the mask that contacts the user. A third module can also contain one or more electrocardiogram (EKG) electrodes to detect heartbeat parameters and to detect heart problems. The third module can also contain piezoelectric transducers or microphones to detect heart activities near the brain. The third module can also contain an ultrasound transmitter and receiver to create an ultrasound model of brain fluids. In one embodiment, an acoustic sensor (microphone or piezoelectric sensor) and an electrical sensor such as an EKG sensor come into contact with the patient or wearer via a conductive gel material. The conductive gel material provides transmission characteristics so as to provide an effective acoustic impedance match to the skin in addition to providing electrical conductivity for the electrical sensor. The acoustic transducer can be directly mounted on the conductive gel material substantially with or without an intermediate air buffer.

In another embodiment, the sensors of the bio-monitoring system or the bio-monitoring system are placed in apposition to the skin immediately adjacent to the medial corner of the eye preferably in the superior aspect of the medial canthal area. The sensor can also be positioned in the medial third of the upper eyelid. The sensor is most preferably located at the main entry point of the tunnel which is located on the skin 2.5 mm medial to the corner of the eye and about 3 mm above the medial corner of the eye. The diameter of the main entry point is about 6 to 7 mm. The positioning of the sensor at the main entry point of the tunnel provides the optimum site for measuring physical and chemical parameters of the person. The bio-monitoring system is preferably secured to the area by having an adhesive backing which lays against the skin, although a combination of adhesive and other means for creating a stable apposition of the bio-monitoring system to the tunnel can be used such as fastening or pressure.

The bio-monitoring system can also comprise a support structure such as clips or structures that are positioned at the end of the tunnel with or without adhesive and which are secured to the area by pressure means.

In an embodiment, the attachable device and the bio-monitoring system can be remotely controlled. In yet another embodiment, the bio-monitoring system is removable. In yet another embodiment, the attachable device is removable.

In an embodiment, the object is washable and reusable. The object can be sterilized or disinfected using a suitable method. In an example, the object can be sterilized by autoclaving. In another example, the object can be sterilized by exposing the object to radiation. The object is portable and easy to use.

In an embodiment, the 3D contoured cup is configured to form a space between the eye and the eye pocket.

In an embodiment, the space can hold a pad on and around the eye.

In an embodiment, the pad is selected from one of a patch, an eye pillow, and a gel pad.

The patch may comprise a herbal layer containing herbal extract which is formed on one surface of a substrate having a specific shape, and an adhesive layer formed on the other surface of the substrate.

The eye pillow may comprise fillers to provide additional therapy. The fillers of the eye pillow may comprise herbs such as flax seed, lavender, chamomile, eucalyptus, and rose.

In an embodiment, the pad may be of the shape of a circle, oval, triangle, quadrangle, pentagon, hexagon, heart, semicircle, or star, which is similar to the eye.

In an embodiment, the pad may be one suitable for applying to a human body, such as paper, polymer film, felt, or fabric.

Figure 6A:
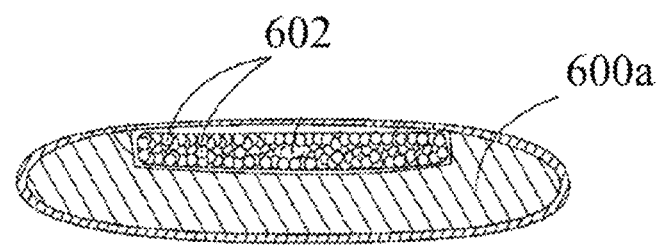
FIG. 6A depicts a gel pad comprising a composition, in one or more embodiments.
Figure 6B:
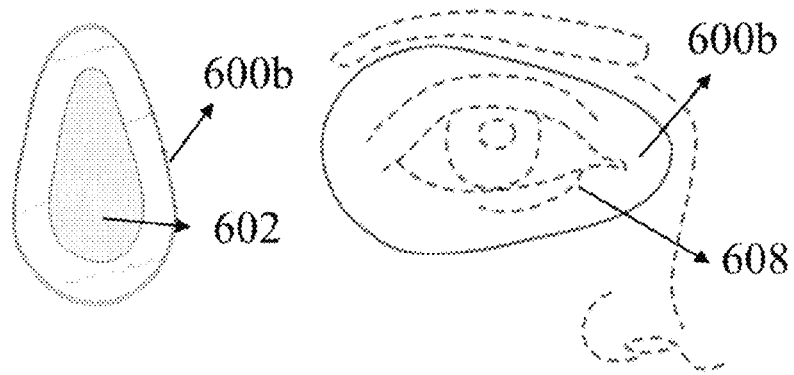
FIG. 6B depicts a patch comprising a composition, in one or more embodiments.

FIG. 6A depicts a gel pad 600a comprising a composition 602 and FIG. 6B depicts an eye patch 600b comprising a composition 602 kept on eye 608, according to one or more embodiments. The gel pad 600a or the eye patch 600b can be kept on or around the eyes by putting it in the spacing provided in between the eye and the eye pocket of the object.

In an embodiment, the pad comprises a nutrient composition.

In an embodiment, the pad comprises a hydrating composition.

In an embodiment, the pad comprises a heating gel.

In an embodiment, the pad comprises a cooling gel.

In an embodiment, the bio-monitoring system comprises at least one of an eye blink sensor and an eye movement sensor.

Figure 7A:
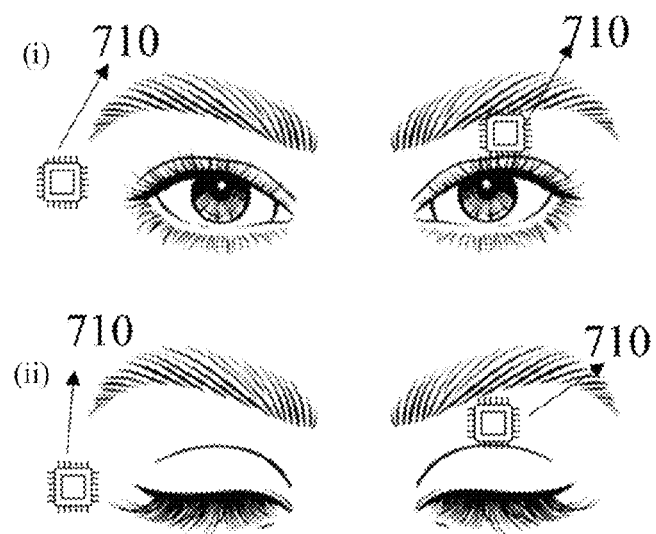
FIG. 7A depicts the sensing of closing and opening of an eye using the biomonitoring system, in one or more embodiments.
Figure 7B:
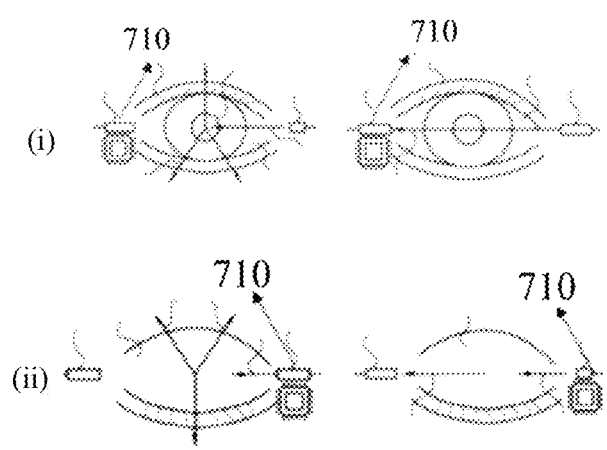
FIG. 7B depicts the sensing of eyeball movement and pupil size in a closed eye and in an open eye biomonitoring system, in one or more embodiments.

FIG. 7A depicts the sensing of closing and opening of an eye using the biomonitoring system 710 comprising the eye blink sensor, in one or more embodiments. FIG. 7B depicts the sensing of eyeball movement and pupil size in an open eye (i) and in a closed eye (ii) by a biomonitoring system 710 comprising the eye movement sensor comprising a camera in one or more embodiments.

Due to the difference in the reflective characteristics of the surface of the eye itself and the eyelid, the intensity of the light reflected off of the eye depends upon whether the eye is open or closed. In an open eye condition, a ray of light produced by the emitter strikes the surface of the eye itself and consequently is scattered. Thus, the resulting light intensity detected by the sensor is relatively low, i.e., the sensor may not receive any substantial return signal. In a closed eye condition or during drowsiness, because the light strikes the eyelid, it is substantially reflected to the sensor, resulting in a relatively high light intensity being detected by the sensor. Alternatively, the beam of light may be broken or cut by the eyelid when the eye is closed.

In an embodiment, the eye blink sensor and the eye movement sensor are highly sensitive and skin attachable. It may be made of a stable flexible piezoelectric thin film. The sensors can detect fatigue and drowsiness, overlong closure, hasty eye blinking, half-closed eyes, and an abnormal eyeball motion.

In some instances, eye movement of one eye or both eyes of the person can be tracked and analyzed. In some instances, both x and y coordinates of eye position for one or both eyes of a person are collected for at least about 100, 500, 1,000, 5,000, 10,000, 50,000, 100,000, 200,000 or more eye positions. In some instances, the eye position is effectively the pupil position. In some instances, the eye movement is tracked for about 30, 60, 90, 100, 120, 150, 180, 200, 220, 240, 270, 300, 360 or more seconds.

The comparison of eye movement of at least one eye of the person to a normal or mean eye movement may feature comparing eye movement of at least one eye of the person to the eye movement of an eye of one or more other people or controls. In some instances, the comparison of eye movement of at least one eye of the person to a normal or mean eye movement may feature comparing the eye movement of both eyes of the person to the eye movement of one or both eyes of one or more other people or controls.

In an embodiment, the bio-monitoring system further comprises at least one of a blood pressure measurement sensor, a pulse measurement sensor, an electrolyte levels measurement sensor, an oxygen level measurement sensor, a glucose level measurement sensor, and a body temperature measurement sensor. In an embodiment, the data collected using the bio-monitoring system can predict the emotional state of a person that includes anger, fear, annoyance, sadness, anxiety, apathy, frustration, distraction, or the like.

In an embodiment, the bio-monitoring system is inbuilt.

In an embodiment, the bio-monitoring system is removable.

In yet another embodiment, the attachable device and the bio-monitoring system can be remotely controlled.

In yet another embodiment, the object comprises a control unit.

Figure 8:
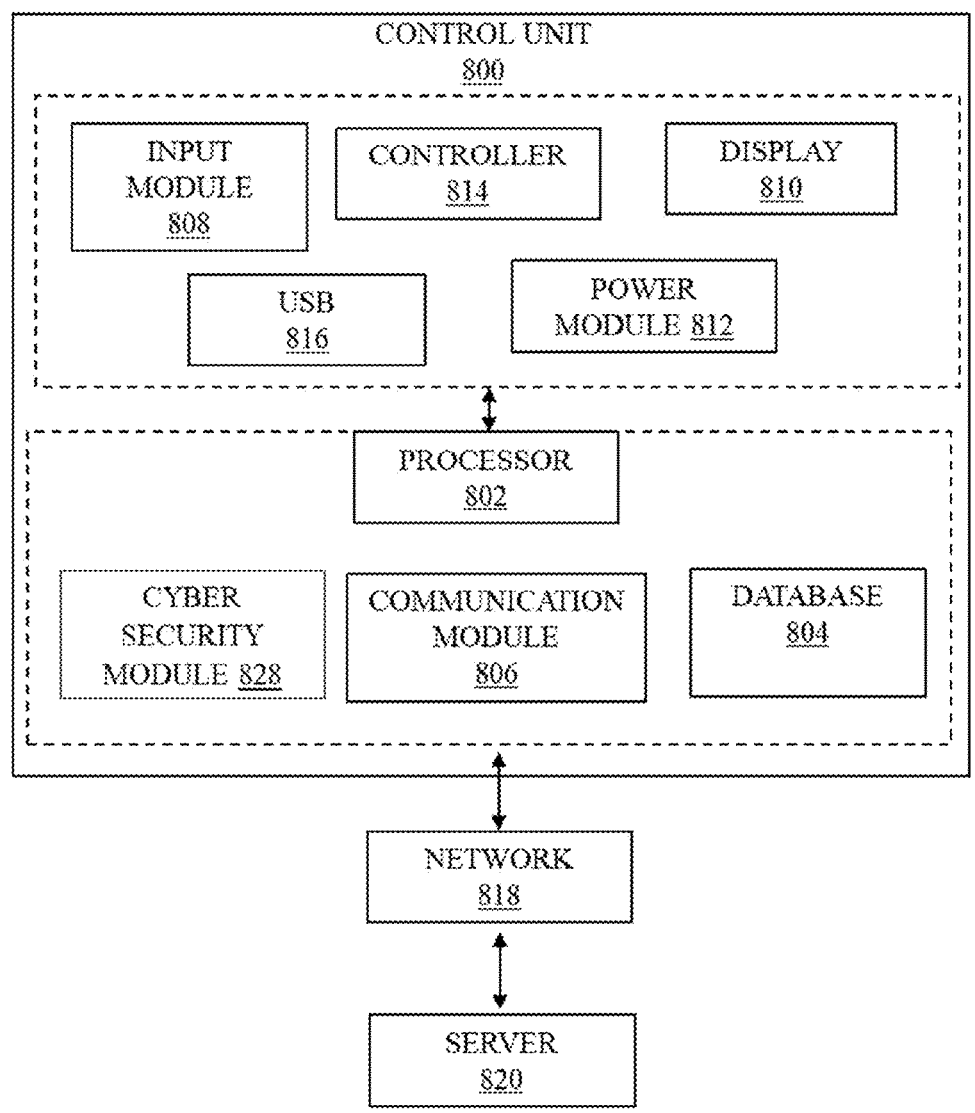
FIG. 8 depicts a control unit of the object, in one or more embodiments.

FIG. 8 depicts a control unit of the object, in one or more embodiments.

In an embodiment, the control unit comprises an input module, a processor, a communication module, a database, a universal serial bus, a controller, a display, and a power module.

The control unit 800 of the object comprises a processor 802, a database 804, a communication module 806, an input module 808, a display 810, a power module 812, a controller 814, a processor, and a universal serial bus (USB) 816. The controller 814 is configured to enable feedback control of a therapy and pulse control circuit for timer control.

The control unit may also comprise a memory. Memory is a computer-readable memory, such as a read-only memory (ROM), random-access memory (RAM), a flash memory, magnetic media memory, and/or other memory for storing data to be used by and/or generated by the object and/or executable program code that may be executed by the data processor.

In an embodiment, the object can communicate data to a server via the communication module. In yet another embodiment, the processor comprises a cyber security module.

In FIG. 8, the control unit 800 further comprises a cyber security module 816 and the communication module 806 communicates to a server 820 via a network 818 using the cyber security module 828.

In an embodiment, the cyber security module further comprises an information security management module providing isolation between the system and the server. In yet another embodiment, the information security management module is operable to: receive data from at least one of the user interface, the bio-monitoring system, the attachable device, and the database; exchange a security key at a start of the communication between the communication module and the server; receive the security key from the server; authenticate an identity of the server by verifying the security key; analyze the security key for a potential cyber security threat; negotiate an encryption key between the communication module and the server; encrypt the data; and transmit the encrypted data to the server when no cyber security threat is detected. In yet another embodiment, the information security management module is operable to: exchange a security key at a start of the communication between the communication module and the server; receive the security key from the server; authenticate an identity of the server by verifying the security key; analyze the security key for a potential cyber security threat; negotiate an encryption key between the system and the server; receive encrypted data; decrypt the encrypted data; perform an integrity check of the decrypted data; and transmit the decrypted data to at least one of the user interface, the bio-monitoring system, the drug dispenser, and the database through the communication module when no cyber security threat is detected. In an embodiment, the integrity check is a hash-signature verification using a Secure Hash Algorithm 256 (SHA256) or similar method.

In an embodiment, the information security management module is configured to raise an alarm when a cyber security threat is detected. In yet another embodiment, the information security management module is configured to discard the encrypted data received if the integrity check of the encrypted data fails. In yet another embodiment, the information security management module is configured to check the integrity of the encrypted data by checking accuracy, consistency, and any possible data loss during the communication through the communication module. In yet another embodiment, the information security management module is configured to perform asynchronous authentication and validation of the communication between the communication module and the server. In yet another embodiment, a perimeter network provides an extra layer of protection. In yet another embodiment, the perimeter network protects the system from a cyber security threat by using a plurality of firewalls.

According to an embodiment, the object provides the display 810 to show a present state of the device and enables a user to define new rules and modify or delete existing rules of an operation. According to an embodiment, the object provides an interface for receiving input for creating and/or modifying rules from computing systems and/or various instruments for monitoring the physiological state of a person. In another embodiment, there can be one or more knobs on the object, for controlling operations of electrical components in the object.

According to some embodiments, the processor 802 is coupled with appropriate user interface peripherals. Various types of computing systems may be used, such as a personal computer system, a laptop computer system, a handheld computer system, or the like.

In an embodiment, the object settings for a patient are stored and retrieved for future automatic setting of the object. All the person (patient) specific data is kept private and secured and all data analytics and aggregation are to be anonymized.

In an embodiment, the power module 812 further comprises one or more of a rechargeable battery, a non-rechargeable battery, a solar cell, a chemical reaction power generator, a power input port that connects to an external power line, or any other device configured to provide power to components of the object.

In an embodiment, the power module 812 is arranged and disposed to provide wireless charging with an induction charger.

In an embodiment, the object can be used as an attachment in an article of furniture.

In an aspect, a method is described herein. The method comprising steps of: providing a therapy to a person using an object; monitoring a physiological state of the person using the object; and estimating an effect of the psychedelic therapy using a bio-monitoring system that monitors a change in the physiological state of the person; and modifying the therapy based on the change in the physiological state; wherein the object comprises a mask comprising a first layer and a second layer adjacent to the first layer; an eye pocket; a speaker; and a bio-monitoring system; wherein the first layer and the second layer form a pouch; and wherein the bio-monitoring system monitors a physiological state of the person.

In an embodiment, the therapy comprises a psychedelic therapy.

In an embodiment, the psychedelic therapy comprises one or more of a psychedelic drug, a light therapy, a sound therapy, an aromatherapy, an acupressure therapy, a massage therapy, and a magnetic therapy.

In yet another embodiment, the bio-monitoring system comprises at least one of an eye blink sensor, an eye movement sensor, a web camera, a blood pressure measurement sensor, a pulse measurement sensor, an electrolyte levels measurement sensor, an oxygen level measurement sensor, a glucose level measurement sensor, and a body temperature measurement sensor. In yet another embodiment, the bio-monitoring system sends data to a biofeedback control system that controls a delivery of a drug to the person.

Figure 9A:
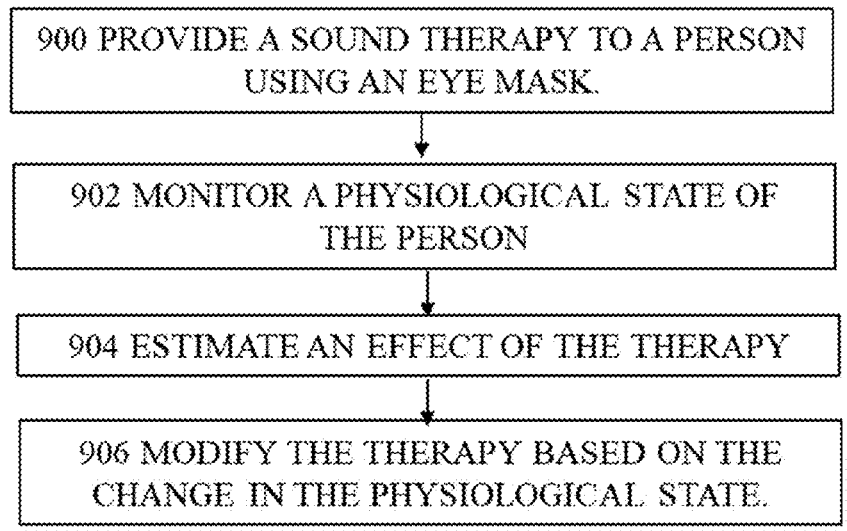
FIG. 9A provides a flow chart of providing a sound therapy and estimating an effect using the object, in one or more embodiments.

FIG. 9A provides a flow chart of providing a sound therapy and estimating an effect using the object, in one or more embodiments. The method comprises the following steps:
  Step 900: Provide a sound therapy to a person using an eye mask.
  Step 902: Monitor a physiological state of the person.
  Step 904: Estimate an effect of the therapy.
  Step 906: Modify the therapy based on the change/s in the physiological state.

Figure 9B:
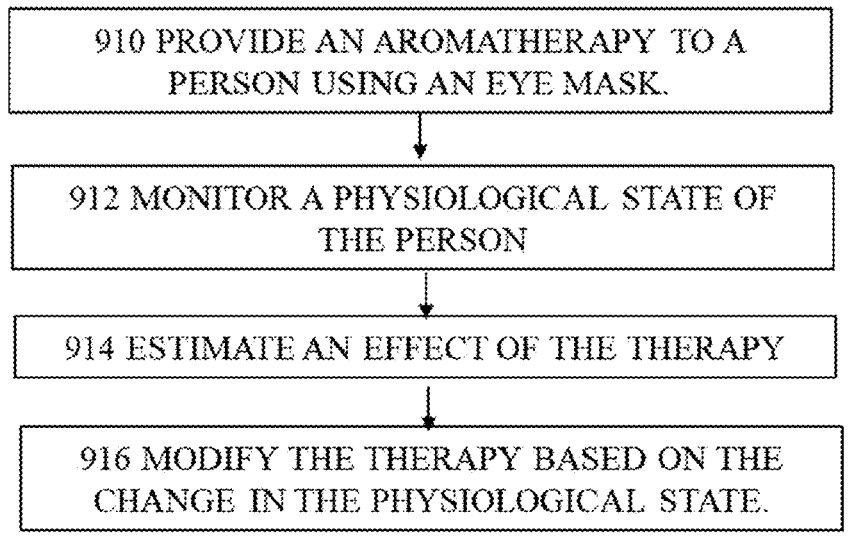
FIG. 9B provides a flow chart of providing an aromatherapy and estimating an effect using the object, in one or more embodiments.

FIG. 9B provides a flow chart of providing an aromatherapy and estimating an effect using the object, in one or more embodiments. The method comprises the following steps:
  Step 910: Provide aromatherapy to a person using an eye mask.
  Step 912: Monitor a physiological state of the person.
  Step 914: Estimate an effect of the therapy.
  Step 916: Modify the therapy based on the change/s in the physiological state.

Figure 9C:
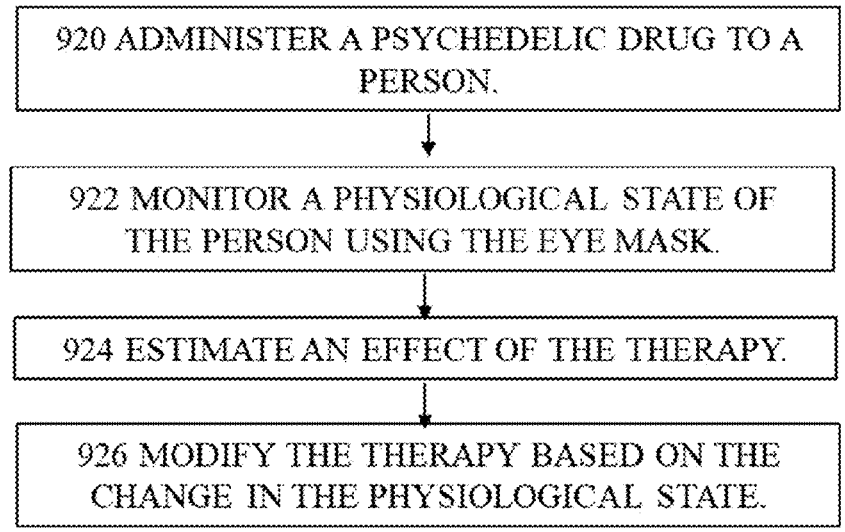
FIG. 9C provides a flow chart of infusing a psychedelic drug to a person and estimating an effect using the object, in one or more embodiments.

FIG. 9C provides a flow chart of infusing a psychedelic drug to a person and estimating an effect using the object, in one or more embodiments. The method comprises the following steps:
  Step 922: Administer a psychedelic drug to a person.
  Step 924: Monitor a physiological state of the person.
  Step 926: Estimate an effect of the psychedelic drug therapy.
  Step 928: Modify the therapy based on the change/s in the physiological state.

Figure 9D:
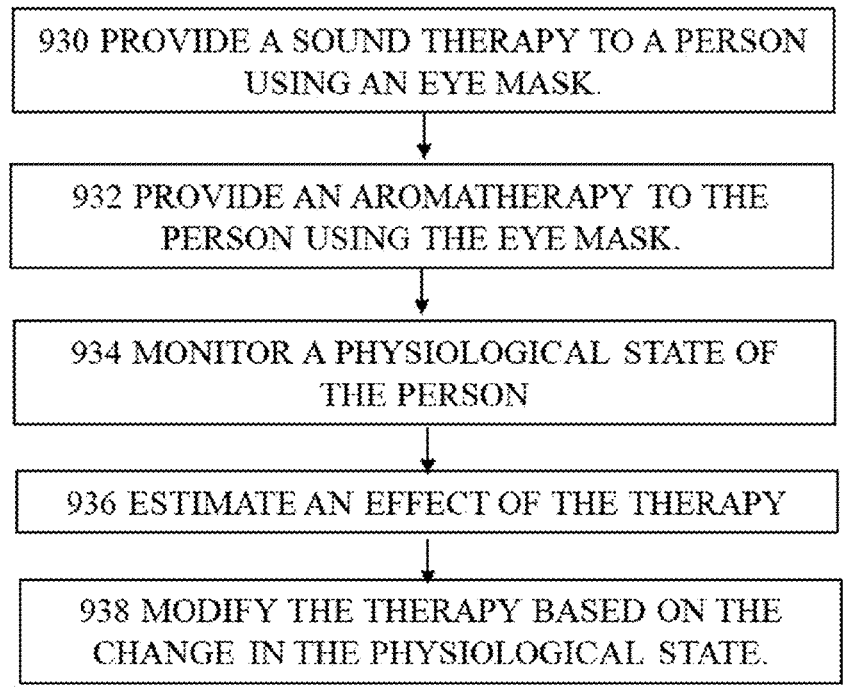
FIG. 9D provides a flow chart of providing an aromatherapy in combination with a sound therapy using the object and estimating an effect using the object, in one or more embodiments.

FIG. 9D provides a flow chart of providing an aromatherapy in combination with a sound therapy using the object and estimating an effect using the object, in one or more embodiments. The method comprises the following steps:
  Step 930: Provide a sound therapy to a person using an eye mask.
  Step 932: Provide an aromatherapy to the person using the eye mask.
  Step 934: Monitor a physiological state of the person.
  Step 936: Estimate an effect of the sound therapy.
  Step 938: Modify the therapy based on the change/s in the physiological state.

Figure 9E:
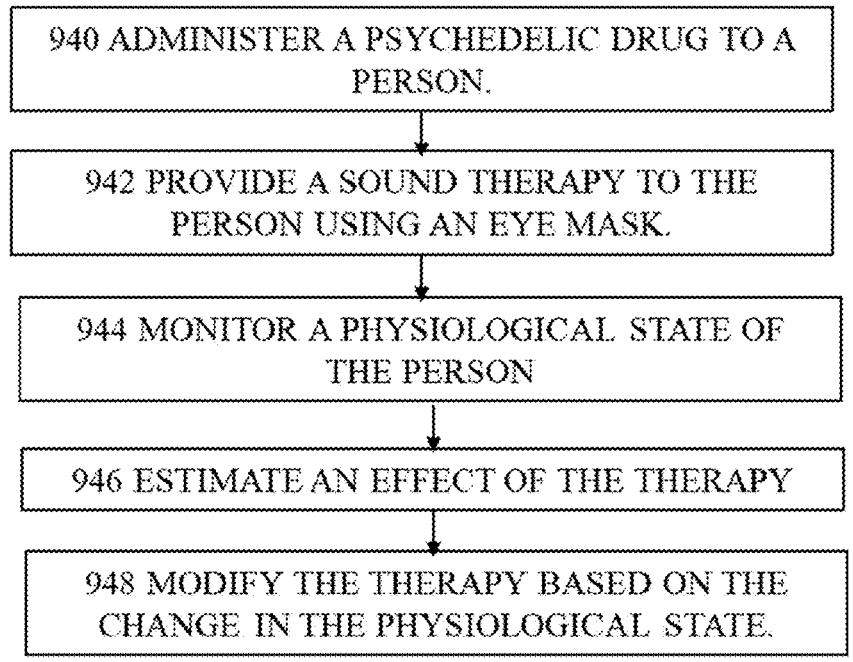
FIG. 9E provides a flow chart of providing a psychedelic drug therapy in combination with an aromatherapy using the object and estimating an effect using the object, in one or more embodiments.

FIG. 9E provides a flow chart of providing a psychedelic drug therapy in combination with an aromatherapy using the object and estimating an effect using the object, in one or more embodiments. The method comprises the following steps:
  Step 940: Administer a psychedelic drug to a person.
  Step 942: Provide a sound therapy to the person using an eye mask.
  Step 944: Monitor a physiological state of the person.
  Step 946: Estimate an effect of the therapy.
  Step 948: Modify the therapy based on the change/s in the physiological state.

Figure 9F:
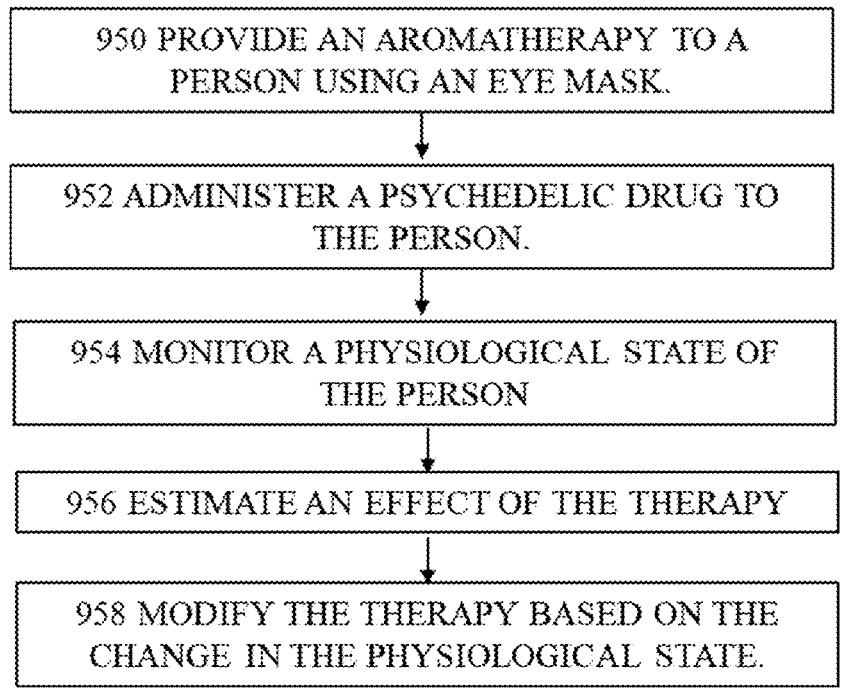
FIG. 9F provides a flow chart of providing a psychedelic drug therapy in combination with a sound therapy using the object and estimating an effect using the object, in one or more embodiments.

FIG. 9F provides a flow chart of providing a psychedelic drug therapy in combination with a sound therapy using the object and estimating an effect using the object, in one or more embodiments. The method comprises the following steps:
  Step 950: Provide an aromatherapy to a person using an eye mask.
  Step 952: Administer a psychedelic drug to the person.
  Step 954: Monitor a physiological state of the person.

Step 956: Estimate an effect of the therapy.

Step 958: Modify the therapy based on the change/s in the physiological state.

Figure 9G:
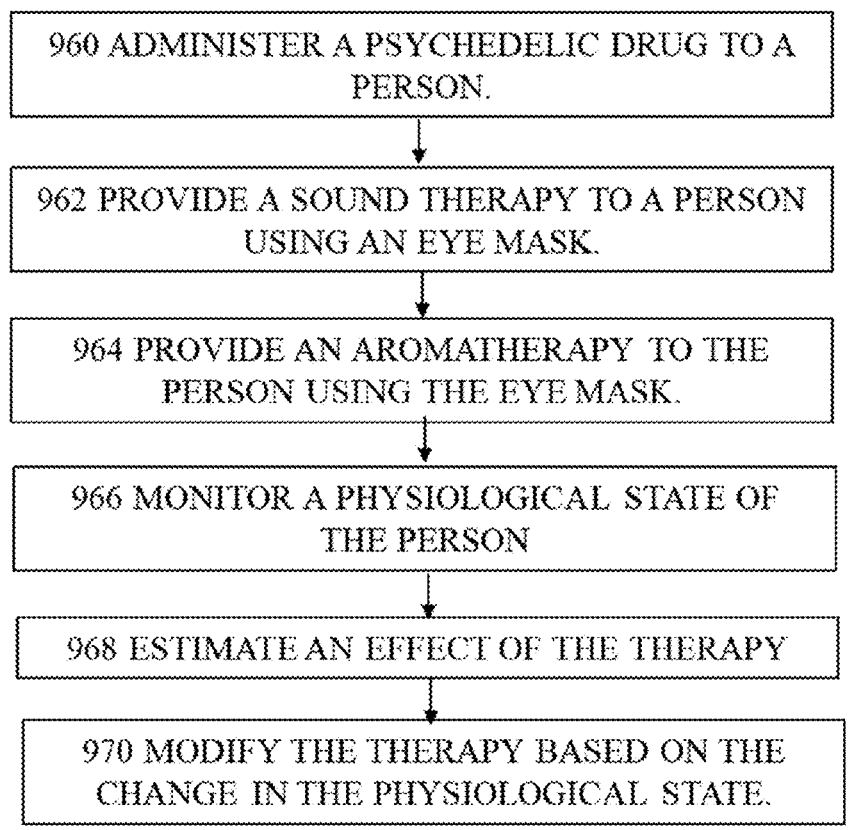
FIG. 9G provides a flow chart of providing a psychedelic drug therapy in combination with a sound therapy and an aromatherapy using the object and estimating an effect using the object, in one or more embodiments.

FIG. 9G provides a flow chart of providing a psychedelic drug therapy in combination with a sound therapy and an aromatherapy using the object and estimating an effect using the object, in one or more embodiments. The method comprises the following steps:

Step 960: Administer a psychedelic drug to a person.

Step 962: Provide a sound therapy to the person using an eye mask.

Step 964: Provide an aromatherapy to the person using the eye mask.

Step 966: Monitor a physiological state of the person.

Step 968: Estimate an effect of the therapy.

Step 970: Modify the therapy based on the change/s in the physiological state.

In an embodiment, the therapy is a psychedelic therapy.

In yet another embodiment, the method further comprises steps of storing data from the bio-monitoring system and the attachable device to a database; securing data access using a cyber security module; accessing the data from the database from a remote location via the cyber security module through authentication; and sending an instruction to the person or a caregiver via a communication module.

In an embodiment, the object may comprise a cyber security module, a communication module, a server, and a database.

In one aspect, a secure communication management (SCM) computer device for providing secure data connections in the healthcare environment is provided. The SCM computer device includes a processor in communication with memory. The processor is programmed to receive, from a first user computer device, a first data message from a user or an attendant. The first data message is in a standardized data format. The processor is also programmed to analyze the first data message for potential cyber security threats. If the determination is that the first data message does not contain a cyber security threat, the processor is further programmed to convert the first data message into a first data format associated with the healthcare environment and transmit the converted first data message to the healthcare system using a first communication protocol associated with the healthcare system.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using security engine including identifying a user device (UD) that incorporates credentials embodied in hardware using a hardware-based module provisioned with one or more security aspects for securing the system, wherein security aspects comprising said hardware-based module communicating with a user of said user device and said HSE.

In an embodiment, there is a cyber security module embedded in each of the layers namely Human Layer, Perimeter Layer, Network Layer, Endpoint Layer, Application Layer, Data Layer, and Mission Critical Layer. Each layer represents a different stage in network communication, from a human typing on a keyboard to the data system used for applications.

Figure 10A:
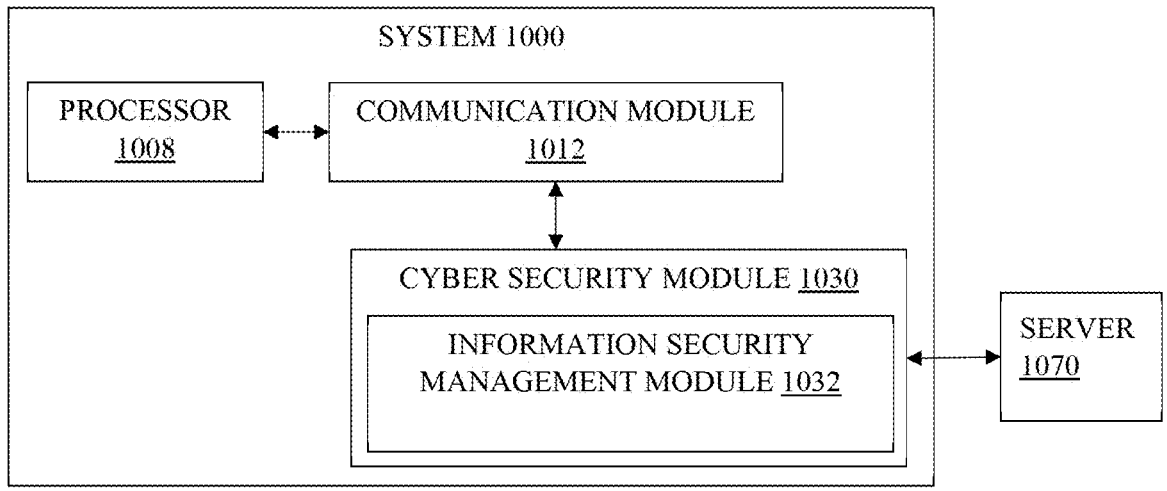
FIG. 10A shows a block diagram of the cyber security module in view of the system and server.

In an embodiment, FIG. 10A shows the block diagram of the cyber security module. The communication of data between the system 1000 and the server 1070 through the communication module 1012 is first verified by the information security management module 1032 before being transmitted from the system to the server or from the server to the system. The information security management module is operable to analyze the data for potential cyber security threats, encrypt the data when no cyber security threat is detected, and transmit the data encrypted to the system or the server.

Figure 10B:
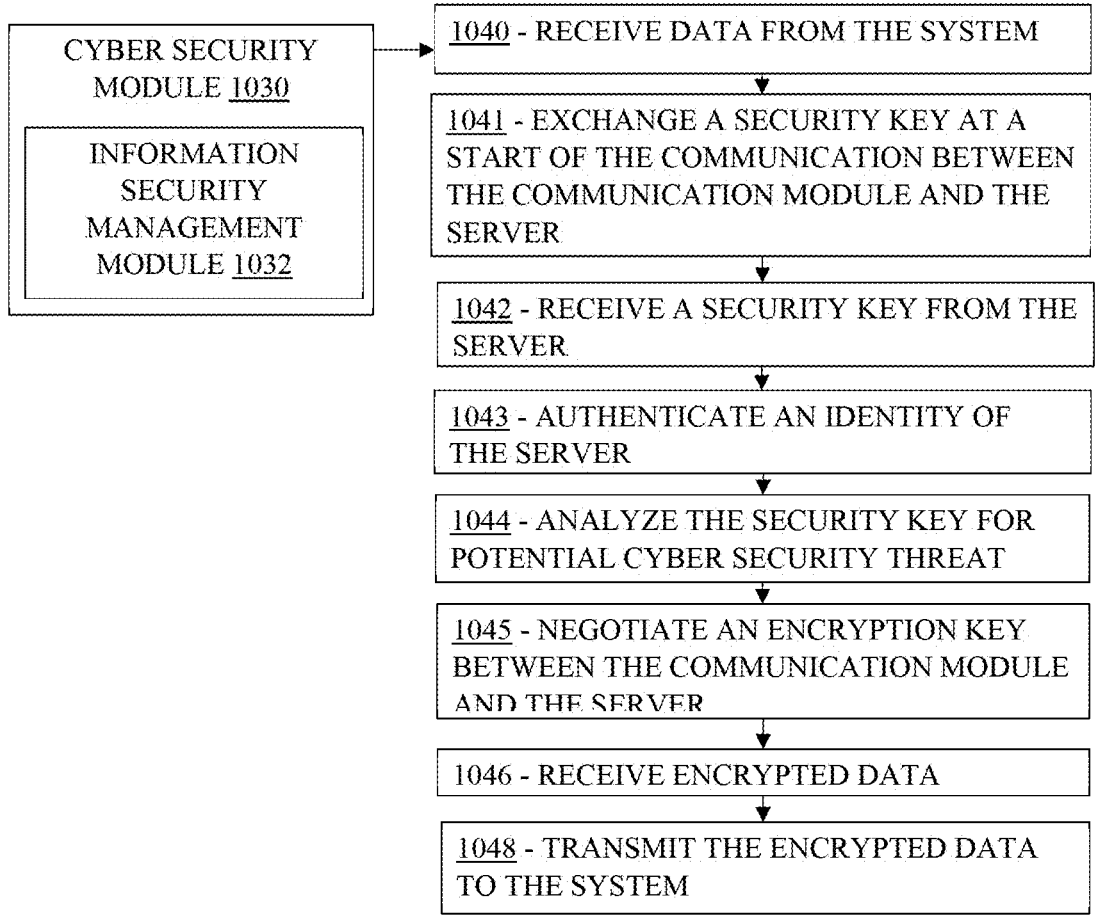
FIG. 10B shows an embodiment of the cyber security module.

In an embodiment, the cyber security module further comprises an information security management module providing isolation between the system and the server. FIG. 10B shows the flowchart of securing the data through the cyber security module 1030. At step 1040, the information security management module is operable to receive data from the system, for example, at least one of an input interface, the drug storage, and the database. At step 1041, the information security management module exchanges a security key at a start of the communication between the communication module and the server. At step 1042, the information security management module receives a security key from the server. At step 1043, the information security management module authenticates an identity of the server by verifying the security key. At step 1044, the information security management module analyzes the security key for potential cyber security threats. At step 1045, the information security management module negotiates an encryption key between the communication module and the server. At step 1046, the information security management module encrypts the data. At step 1047, the information security management module transmits the encrypted data to the server when no cyber security threat is detected.

Figure 10C:
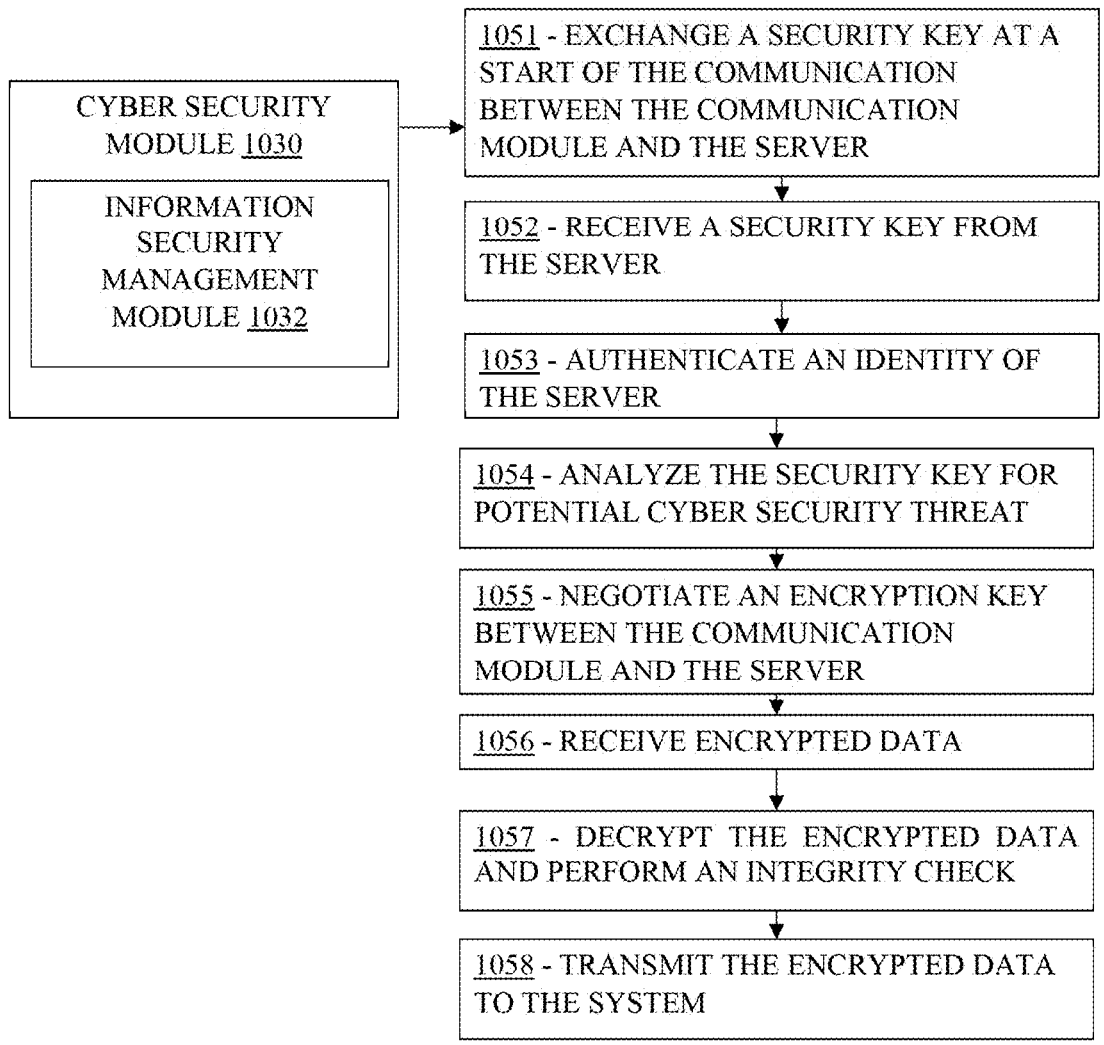
FIG. 10C shows another embodiment of the cyber security module.

In an embodiment, FIG. 10C shows the flowchart of securing the data through the cyber security module 1030. At step 1051, the information security management module is operable to: exchange a security key at a start of the communication between the communication module and the server. At step 1052, the information security management module receives a security key from the server. At step 1053, the information security management module authenticates an identity of the server by verifying the security key. At step 1054, the information security management module analyzes the security key for potential cyber security threats. At step 1055, the information security management module negotiates an encryption key between the system and the server. At step 1056, the information security management module receives encrypted data. At step 1057, the information security management module decrypts the encrypted data, performs an integrity check of the decrypted data. At step 1058, the information security management module transmits the decrypted data to the system, for example, at least one of output interface, drug storage, and the database through the communication module when no cyber security threat is detected.

In an embodiment, the integrity check is a hash-signature verification using a Secure Hash Algorithm 256 (SHA256) or a similar method. A cryptographic hash (sometimes called 'digest') is a kind of 'signature' for a text or a data file. SHA256 generates an almost-unique 256-bit (32-byte) signature for a text.

In an embodiment, the information security management module is configured to perform asynchronous authentication and validation of the communication between the communication module and the server.

In an embodiment, a perimeter network provides an extra layer of protection. In an embodiment, the perimeter network protects the system from a cyber security threat by using a plurality of firewalls. Usually, a perimeter network is the final step a packet takes traversing one of the system's networks on its way to the internet; and conversely the first network encountered by incoming traffic from the Internet to the system.

In an embodiment, a demilitarized zone (DMZ) network functions as a subnetwork containing an organization's exposed, outward-facing services. It acts as the exposed point to an untrusted network, commonly the Internet. A DMZ network will add an extra layer of security to an organization's local area network. It is a protected and monitored network node that faces outside the internal network and can access what is exposed in the DMZ, while the rest of the organization's network is safe behind a firewall. A DMZ Network gives organizations extra protection in detecting and mitigating security breaches before they reach the internal network, where valuable assets are stored. All services accessible to users on communicating from an external network can and should be placed in the DMZ, if one is used. The most common services include, but are not limited to, web servers, mail servers, file transfer protocol (FTP) servers.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, the server is physically isolated from the system through the information security management module. When the system communicates with the server as shown in FIG. 10A, identity authentication is firstly carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed. Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key needs to be bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adopting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed.

In an embodiment, the identity authentication is that both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting an Rivest-Shamir-Adleman (RSA) encryption algorithm. RSA is a public-key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, integrity check calculation is carried out on the data, the calculated Message Authentication Code (MAC) value is added with the head of the value data message, then the data (including the MAC of the head) is encrypted by using a 3DES algorithm, the head information of a security layer is added after the data is encrypted, and then the data is sent to the next layer for processing.

In an embodiment the next layer refers to a transport layer in the Transmission Control Protocol/Internet Protocol (TCP/IP) model.

In an embodiment, when the receiving side finds an authentication error or a MAC decryption error, it is necessary to send a fatal error message to the transmitting side and close the connection.

The information security management module ensures the safety, reliability, and confidentiality of the communication between the system and the server through the identity authentication when the communication between the two communication parties starts the data encryption and the data integrity authentication in the communication process. The method is particularly suitable for an embedded platform which has less resources and is not connected with a Public Key Infrastructure (PKI) system and can ensure that the safety of the data on the server of the drug storage cannot be compromised by hacker attack under the condition of the Internet by ensuring the safety and reliability of the communication between the system and the server in the system for smart storage.

In an embodiment, a system hardening strategy is implemented to prevent at least one attack. An attack graph analysis may be used to help analyze network vulnerability. Once an attack graph of conditions and/or exploits (e.g., at least one goal condition, at least one initial condition, at least one exploit) is obtained, allowable actions that may harden the conditions may be obtained. Costs associated with the allowable actions may also be obtained. Recommended actions to harden the network with respect to one or more goal conditions may be determined.

Figure 11:
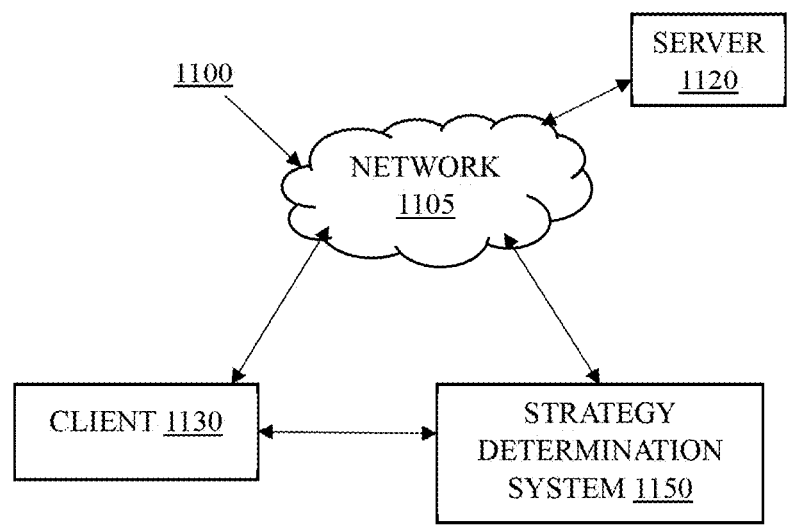
FIG. 11 is an example system where a system hardening strategy may be implemented according to an embodiment of the invention.

FIG. 11 is a system 1100 according to an embodiment of the invention. In this example, the system 1100 may comprise a network 1105 (e.g., the Internet, an intranet) wherein one or more computers 1120 (e.g., server, client) may communicate with one another. A strategy determination system 1150 may communicate with the client and/or the server. The strategy determination system 1150 may obtain an attack graph of conditions and/or exploits (e.g., using known techniques), obtain allowable actions that may remove one or more initial conditions to harden the network with respect to one or more goal conditions; obtain costs associated with the allowable actions, and determine recommended system hardening strategies to efficiently harden the network with respect to the goal condition(s), each system hardening strategy consisting of one or multiple allowable actions. As attackers may leverage complex interdependencies of network configurations and vulnerabilities to penetrate seemingly well-guarded networks, in an embodiment, the recommended actions may consider attacker exploits in isolation and/or in combination. Attack graphs may reveal such threats by enumerating potential paths that attackers can take to penetrate networks. This may help determine whether a given set of system hardening measures provides safety for given critical resources.

System hardening goal conditions may have a corresponding impact on removing paths in the attack graph. In addition, system hardening solutions that are optimal with respect to some notion of cost and/or time may be determined. Such system hardening solutions prevent the attack from succeeding, while minimizing the associated costs.

The strategy determination system 1150 may comprise: a determine allowable actions module; an associate costs module; a determine recommended actions module; or an approximation module; or any combination thereof. In the strategy determination method, an attack graph comprising conditions and/or exploits may be obtained, allowable actions that remove one or more initial conditions may be obtained, costs associated with the allowable actions may be obtained, and recommended strategies comprising allowable actions may be determined based upon costs and/or time constraints.

Spyware is a type of malware that may be installed on computers and collects bits of information at a time about users without their knowledge. The presence of spyware is typically hidden from the user and may be difficult to detect. Spyware programs may collect various types of personal information, such as Internet surfing habits and sites that have been visited but may also interfere with user control of the computer in other ways, such as installing additional software and redirecting Web browser activity.

Figure 12:
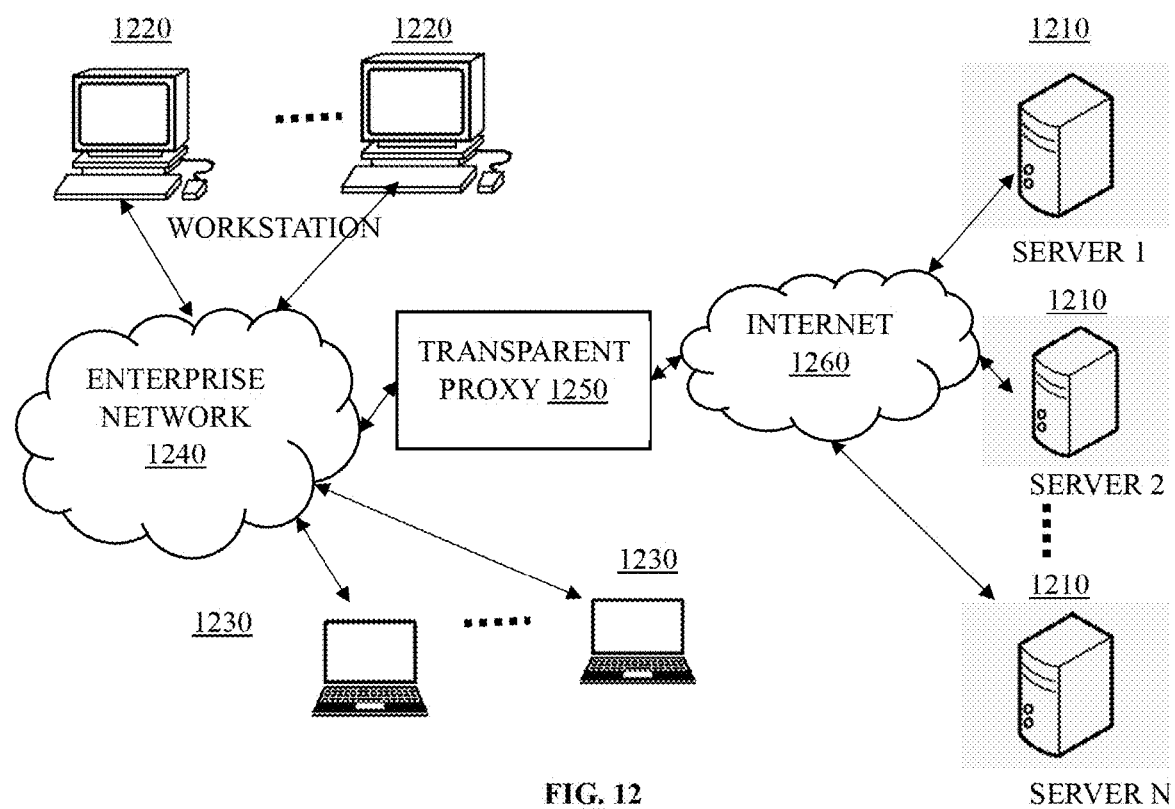
FIG. 12 shows an architecture of a network using a transparent proxy in an Enterprise network as per an aspect of an embodiment of the present invention for active malware detection.

Passive detection may identify a fraction of the malware that is collected in an enterprise network but may not identify all of them. Embodiments of the present invention utilize active detection mechanism(s). The active detection mechanism(s) may also be called Active Content Challenges and may be implemented using a transparent proxy. FIG. 12 shows the architecture of a network using an embodiment of the transparent proxy 1250 in an Enterprise network 1240 including workstations 1220 and laptops 1230. The architecture may be fully transparent and may not require any application or network modifications both for client applications and servers and may accommodate various protocols including HTTP, encrypted HTTP (HTTPS) and Voice over IP (VOIP) protocols. The transparent proxy 1250 may mediate all traffic both encrypted and unencrypted when an application initiates a communication with a server 1210 connected to Internet 1260 outside the enterprise. Communication may pass through the firewall while being examined and analyzed by the transparent proxy 1250. According to an embodiment, a transparent proxy may be in a laptop or workstation. The transparent proxy may mediate all traffic both encrypted and unencrypted when an application initiates a communication with a remote server connected to the internet.

The transparent proxy 1250 may intercept outbound requests and issue Active Content Challenges to the requesting application. The principle is similar to Turing puzzles and Captchas, however, rather than trying to distinguish a human from software, the objective is to distinguish legitimate software from malware. Thus, unlike existing mechanisms that demand end-users to be involved in the identification process by solving a puzzle, the approach in this embodiment requires no user involvement or application modification. The transparent proxy for malware detection may include a monitor module, a protocol determination module, a challenge generation module, a response determination module, and a data control module. The transparent proxy may include interfaces for receiving and transmitting applications traffic and remote server traffic. The transparent proxy may be located on a network edge or on a laptop or workstation and may examine outgoing traffic. In general, the approach frustrates the communication of the malware by injecting traffic that the malware is incapable of parsing and generating a valid response contrary to the legitimate application.

In an embodiment, a secure virtual browsing environment is provided which includes creating a virtual browsing environment with a virtualized operating system sharing an operating system kernel of a supporting operating system and executing the browser application within the virtual browsing environment. Another embodiment includes receiving a website selection within a browser application, determining if the website selection corresponds to a secure bookmark, and creating a second virtual browsing environment and executing the browser application within the second virtual browsing environment to access the website selection when the website selection corresponds to a website specified as a secure bookmark. Another embodiment includes monitoring operation of the operating system within the at least one virtual browsing environment, determining when the operation of the operating system includes potential malicious activity, and terminating the virtual browsing environment when the operation includes potential malicious activity.

Figure 13A:
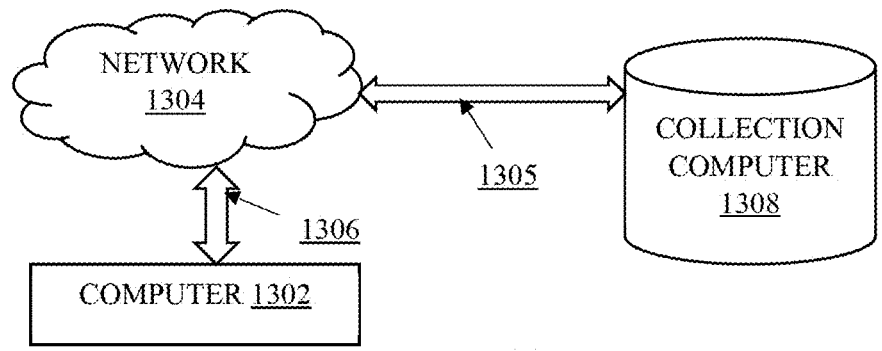
FIG. 13A illustrates a system for providing a virtual browsing environment according to an aspect of an embodiment of the invention.

FIG. 13A illustrates a system 1300 for providing a virtual browsing environment according to one embodiment of the invention. As described below, embodiments of the system 1300 may provide a virtual browsing environment for executing a browser application on a computer. By executing the browser application within a separate virtual browsing environment, other applications, data, and modules of the computer may be protected from any malicious activity associated with the execution of the browser application. In addition, because in some embodiments only the browser application may be executed within the virtual browsing environment, malicious activity associated with the execution of the browser application may be easily detected. The system 1300 may include at least one computer 1302, at least one network 1304, and at least one collection computer ("CC") 1308 and other components. The computer 1302 and the network 1304 may be connected by a connection 1306, and the network 1304 and the collection computer 1308 may be connected by a connection 1305. The collection computer 1308 may receive data from the network 1304 over the connection 1305. In some embodiments, the collection computer 1308 may also send data to the network 1304 or one or more computers or networks. The collection computer 1308 may also include hardware, such as one or more memory modules, one or more processors, and one or more input/output modules. In addition, the collection computer 1308 may include an operating system to manage the hardware. In some embodiments, the collection computer 1308 may also include a database that stores data received from the network 1304. The data included in the database may be stored in the collection computer's 1308 one or more memory modules, and the data may be managed by a database management application.

Figure 13B:
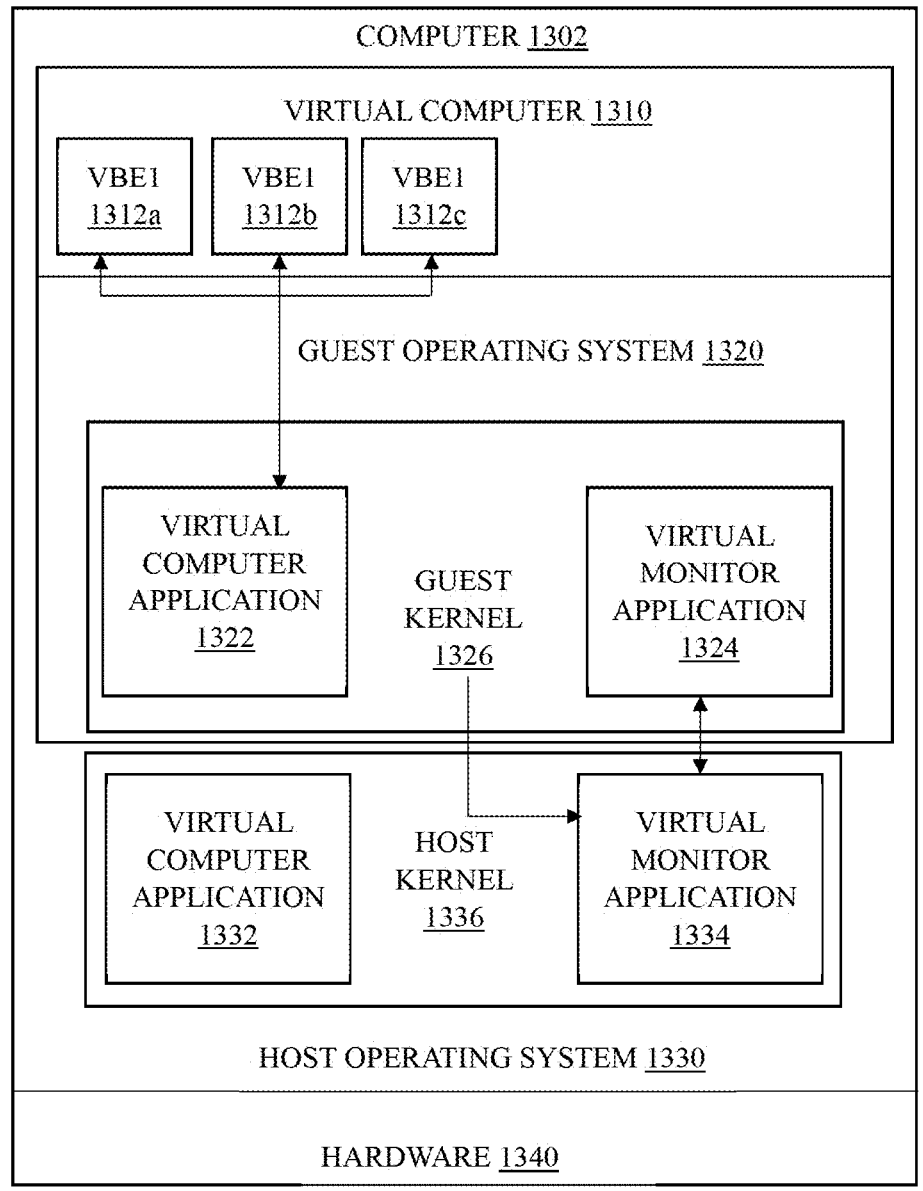
FIG. 13B illustrates a computer included in the system of FIG. 13A, according to an embodiment of the invention.

FIG. 13B illustrates the computer 1302 of FIG. 13A which includes a host operating system 1330 that provides an interface between the hardware 1340 and a user operating the computer 1302. The host operating system 1330 may be stored in the one or more memory modules and may be executed on the one or more processors included in the hardware 1340. The host operating system 1330 may include at least one host kernel 1336. The host kernel 1336 may manage the communication between the hardware 1340 and applications executed by the hardware 1340. The host kernel 1336 may use the virtual control application (VCA) 1334 to create and manage a virtual computer. Accordingly, the VCA 1334 may provide virtualization functionality. The host kernel 1336 may also include a shared preference directory 1332, which may store preferences for an application, such as a browser application. It should be understood that the one or more memory modules included in the hardware 1340 may store other applications besides those explicitly shown in FIG. 13B. In addition, the functionality provided by the applications stored in the one or more memory modules may be combined and distributed in various configurations.

In operation, as shown in FIG. 13B, the host kernel 1336 may execute the VCA 1334 to create a virtual computer 1310. The virtual computer 1310 may include its own guest host operating system 1320 with a guest kernel 1326. The guest operating system 1320 and guest kernel 1326 may operate similar to the host operating system 1330 and host kernel 1336. This type of virtualization where a generally complete copy of an operating system is provided within a virtual computer is generally referred to as "full virtualization." Outside of the virtual computer 1310, the host operating system 1330 may continue to interact and manage the hardware 1340, while the guest operating system 1320 also may interact and manage the hardware 1340. Therefore, the virtual computer 1310 may create a second, isolated computing environment within the computer 1302. Each computing environment may execute different applications, access data from different locations in a memory module or from different memory modules, provide different operating systems, or combinations thereof. Creating the virtual computer 1310 may provide isolation between computing performed within the virtual computer 1310 and computing performed outside the virtual computer 1310 through the host operating system 1330. For example, the virtual computer 1310 may be unaware of any computing performed outside of the virtual computer 1310. Accordingly, an application executed within the virtual computer 1310 generally cannot access an application executed outside the virtual computer 1310.

As shown in FIG. 13B, the guest kernel 1326 may include a virtual computer control application ("VCCA") 1322 and a virtual computer monitor application ("VCMA") 1324. The VCCA 1322 may manage the operation of the virtual computer 1310. For example, as shown in FIG. 13B, the VCCA 1322 may create one or more virtual browsing environments ("VBE") 1312 (e.g., VBE 1 1312 *a*, VBE 2 1312 *b*, and VBE 3 1312 *c*). Once created, the VCMA 1324 may monitor the operation of each VBE 1312 and may report each VBE's operation to the VCA 1334. To create a VBE 1312, the VCCA 1322 may use one or more virtualization modules or applications, such as OpenVZ, UnionFS patches, Solaris Zones, BSD Jail, or combinations thereof.

It is known that internet-enabled applications run side-by-side with all other desktop and system software with the privileges of the user. As a result, when a compromise occurs through the Internet, the entire system can be compromised by a single vulnerability in an Internet-enabled software such as a Web browser or an email client. By simply browsing to a Web page, a user can compromise their system, sometimes irreversibly.

In an embodiment, the system works by launching a virtual machine for each Internet-enabled or untrusted application that is started. The virtual machine provides a pristine guest operating system (OS) for the Internet-enabled or untrusted application that is launched. This operating system may be an operating system unmodified from the original version delivered by the manufacturer or another version suitably configured for the task of running intended applications. The virtual machine and its guest operating system may be temporally limited to exist only for the duration of the session of the application. When the user exits the application, the virtual machine can be destroyed. For the duration of the session, the virtual machine provides an isolated environment from the host machine from which it is launched. The virtual machine provides a level of isolation from the host machine that is the equivalent to running a physically separate machine from the host machine. Any attacks that occur on the machine via an Internet connection can compromise only the virtual machine that is started up for that session. When the session is terminated, so is the virtual machine and the compromise. With each new session, a pristine new virtual machine is started up, meaning that any malicious software that was downloaded or planted during a prior session is no longer present. The underlying host operating system does not need to maintain an Internet connection. As a result, Internet-based attacks have a very limited ability to compromise the host operating system.

Figure 14:
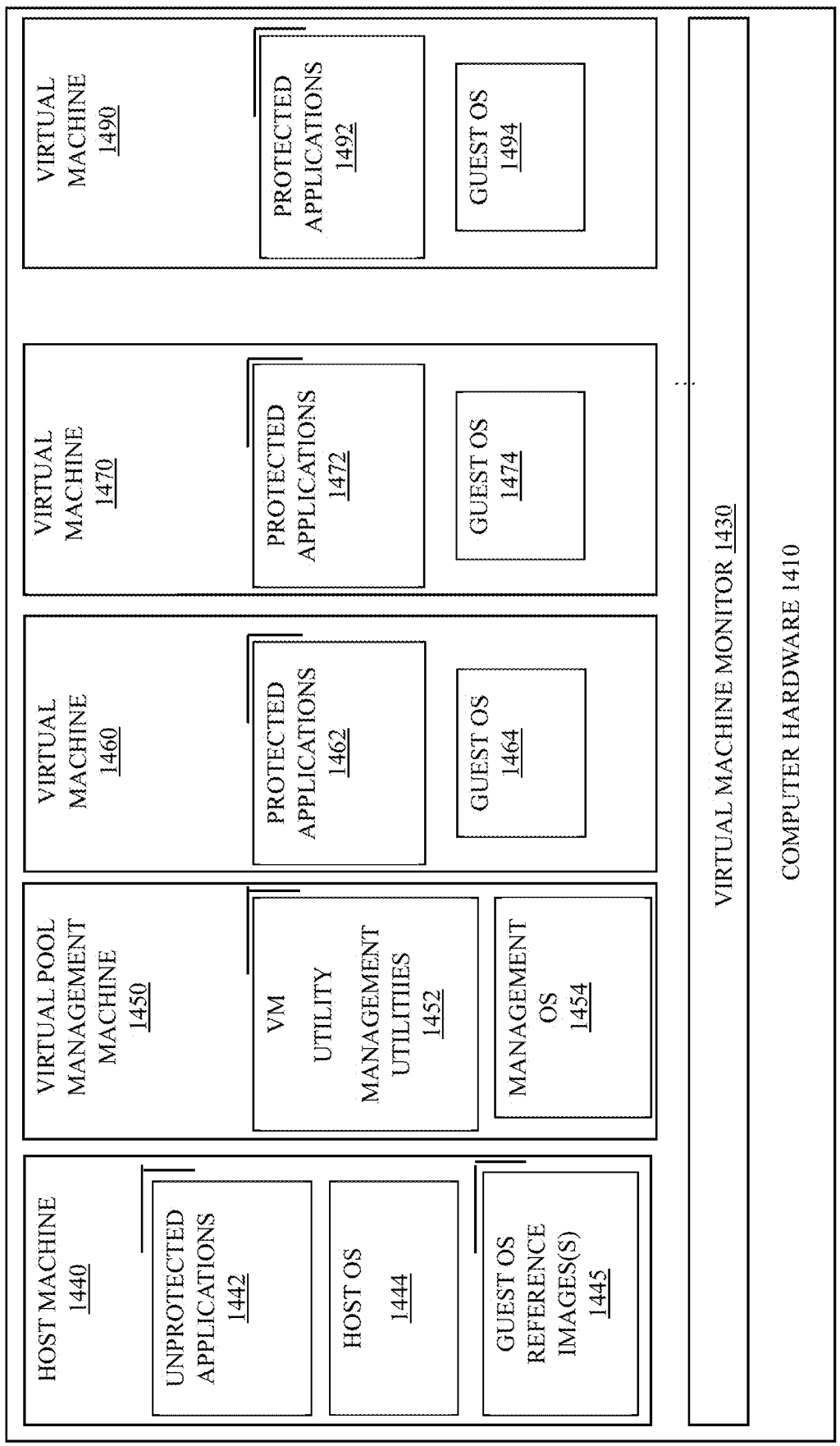
FIG. 14 is a block diagram of a virtual machine architecture of an aspect of an embodiment of the present invention to prevent malicious software attack.

According to an embodiment, an architecture shown in FIG. 14 uses the standard virtual machine architecture with the Virtual Machine Monitor (VMM) 1430 running on the computer hardware 1410, and host operating systems (1444, 1454, 1464, 1474, and 1494) running on top of the VMM 1430. A host operating system (OS) 1444 is defined as the default machine the user normally uses and is the machine whose desktop is presented to the user. Guest OSs (1464, 1474 and 1494) are created by request when a protected application (1462, 1472 and 1492) is launched, or created in advance to enable higher performance when launching protected applications (1462, 1472 and 1492) into pre-instantiated guest OSs (1464, 1474 and 1494). A Management VM 1450 may be bootstrapped along with the Host OS 1444 and a reference guest OS image 1445 that is used for clones of the guest OS reference image 1445. The Management VM 1450 is used for command, control, and lifecycle maintenance of the guest OSs (1464, 1474 and 1494) based on the instructions from the host OS 1444. The number of guest OSs instantiated may be dependent on the number of protected applications launched and the performance limits of the underlying hardware. The VMM 1430 and VM 1450 should support live capture of the full system state in a file for subsequent replay. This file is called a "snapshot" of system state.

The host operating system 1444 may be configured for higher security so that it is unable to make Internet connections itself. The guest operating systems (1464, 1474 and 1494) may be free to make direct Internet connections; however, they should be restricted from freely accessing the host operating system 1444 by the virtual machine monitor 1430 that runs in its own hardware protection domain which provides hardware-equivalent strong isolation between the virtual machine and its host operating system. The guest operating systems (1464, 1474 and 1494), which are pristine builds of the OS, should also be "root secure", which means that even if one of the guest operating systems (1464, 1474 and 1494) is compromised to a root user level or the kernel itself is compromised, the host operating system 1444 itself should not be compromised by the compromised guest operating system. Once a guest operating system is destroyed (upon closure of the protected application that started the guest OS), the compromise is now removed from the system.

As mentioned earlier, a reference guest OS image 1445 may be booted along with the host OS 1444. A snapshot of the reference guest OS image 1445 may be taken, then used to derive subsequent VM images by cloning it, i.e., creating a replica image of the reference guest OS. When a new untrusted application is to be started, a dispatch instruction is sent from the Host OS to the Virtual Pool Management Machine 1450, which then creates a VM for the application using the reference guest OS image, if the VM has not already been created. By cloning and pre-booting reference images, the response time for instantiating the application should be on par or even faster than the usual response time for starting a new application for users.

As described, FIG. 14 shows an embodiment of the present invention where virtual machines (VM) monitor 1430 runs directly on computer hardware 1410. In this embodiment, every host machine (1440, 1450, 1460, 1470 and 1490) is essentially a guest machine to the computer hardware. In this setup, the unprotected host applications 1442 run on the host machine 1440 natively and the host operating system 1444 runs these unprotected host applications 1442. In contrast, the guest virtual machines 1460, 1470 and 1490 run protected applications (1462, 1472, and 1492 respectively) that may talk to a network under guest operating systems (1464, 1474 and 1494 respectively).

The guest operating systems 1464, 1474, and 1494 are each cloned from one of the guest operating system images(s) 1445, and the images 1445 should be pristine snapshots of a running operating system. To increase speed, the snapshots may also include running applications. For example, an image 1445 of an operating system for an email virtual machine can include a copy of an email application running under the operating system.

The virtual pool management machine 1450 runs a series of virtual machine management utilities 1452 under a management operating system 1454. These utilities 1452 include functions that: create, destroy, put to sleep, and wake up virtual machines. The utilities also maintain a list that matches applications to virtual machines. In other embodiments, these same functions may be performed by pool management utilities running on a host machine.

Figure 15:
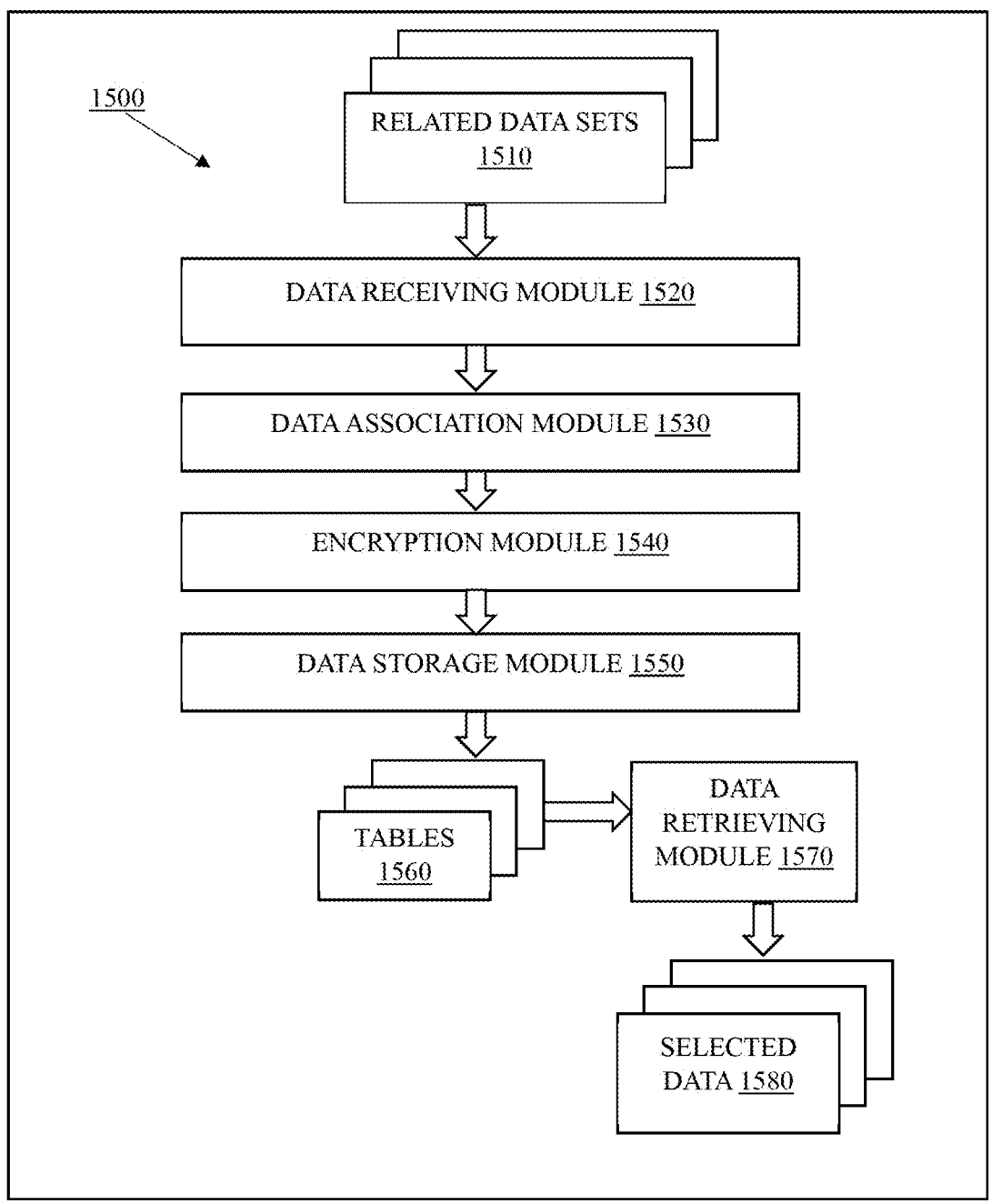
FIG. 15 is a block diagram for securing sensitive data associations for related data values of an aspect of an embodiment of the present invention.

In an embodiment, sensitive data associations for related data values are protected. FIG. 15 is a block diagram of a system 1500 for protecting sensitive data associations according to an aspect of an embodiment of the present invention. The block diagram shows a multitude of modules. As shown, the system includes a data receiving module 1520 configured to receive a set(s) of related data values 1510. The set(s) of related data values 1510 preferably include at least a first data value and a second data value. The system normally operates against rule(s) that indicate which data value associations need to be kept secret. In the absence of such a rule, a default rule may be used such as the association of the first data value and the second data value needs to be kept secret.

A data association module 1530 may be configured to associate the first data value to a first data field; and the second data value to a second data field. An encryption module 1540 may then create first encrypted data by encrypting the first data value using a first encryption key; and create second encrypted data by encrypting the second data value using a second encryption key. A data storage module 1550 is configured to store: the first data value in a first data table 1560; the second data value in a second data table 1560; the first encrypted data in the second table 1560; and the second encrypted data in the first table 1560.

A data retrieving module(s) 1570 may be used to retrieve: the first data value by decrypting the first encrypted data using a first decryption key and/or the second data value by decrypting the second encrypted data using a second decryption key. As with the method embodiments, there are many possibilities for the encryption and decryption keys. The encryption key and the decryption key may be the same symmetric key. The encryption keys may be different or the same. Similarly, the decryption keys may be the same or different. The choice of keys should be made carefully to ensure that the data relationships in the rule(s) be kept secret. In some embodiments, the rule may be received from an external source. In the absence of an external rule, an internal rule or a default rule may be used.

In an embodiment, there is a tool for storing data records in a data store that is scalable and that allows a user to define their encryption and relieves a user from the task of managing keys used for data security. In an embodiment, application data and associated encryption key(s) are stored on at least k+1 remote servers using linear hashing (LH*) addressing. At least k+1 buckets are created on separate remote servers. At least k+1 key shares are generated for each of at least one encryption key. Each encryption key has a unique key number. Each key share is stored in a different key share record. Each of the key share records is stored in a different bucket using LH* addressing. Encrypted application data is generated by encrypting the application data with the encryption key(s). The encrypted application data is stored in encrypted data record(s). Each of the encrypted data records is stored in a different bucket among the buckets using LH* addressing.

Figure 16:
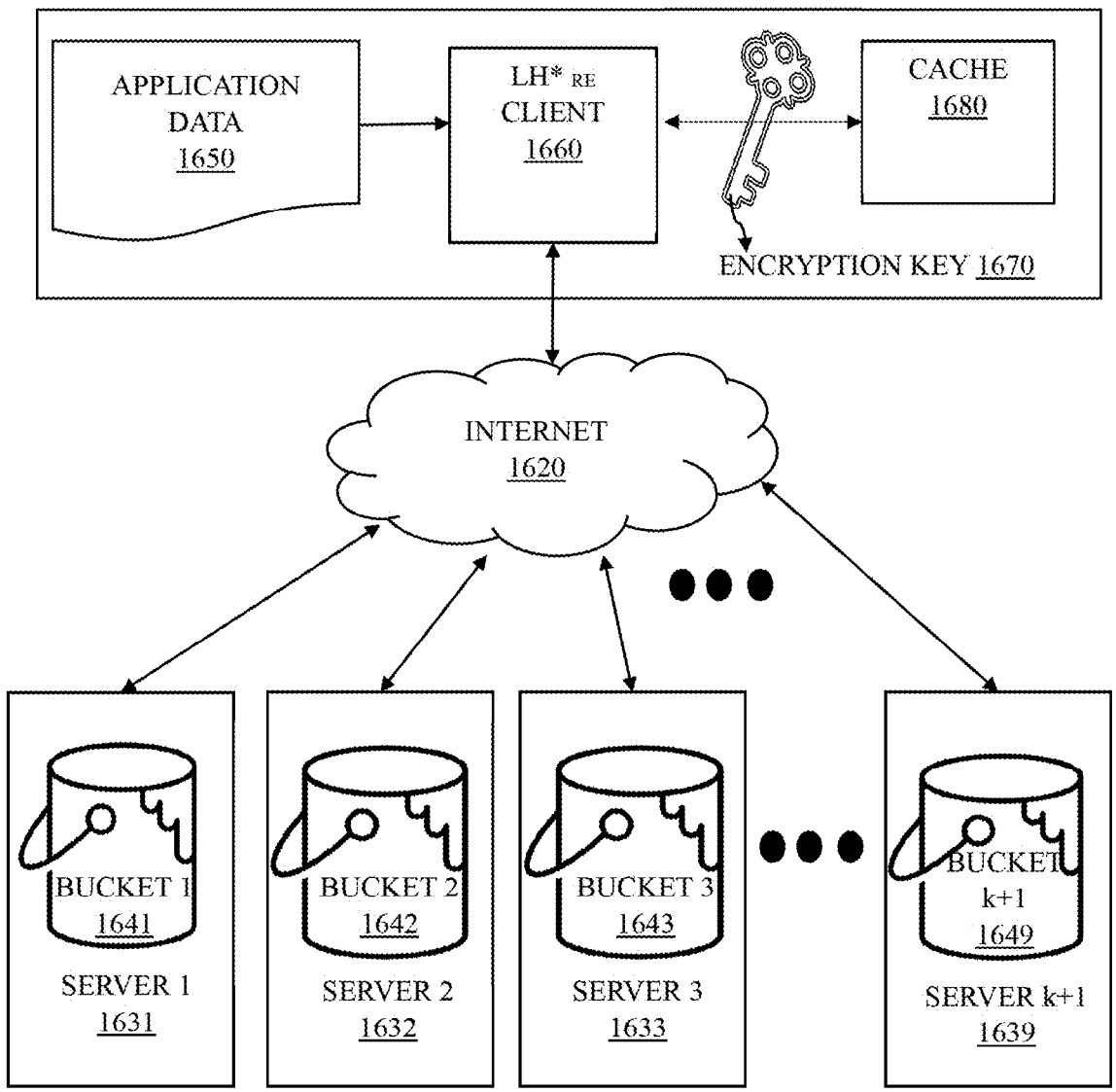
FIG. 16 is a system block diagram showing an example client interacting with k+1 servers that allows a user to define their encryption and relieves a user from the task of managing keys used for data security, as per an aspect of an embodiment of the present invention.

FIG. 16 is a system block diagram showing an example client 1610 interacting with k+1 remote servers (1631, 1632, 1633, . . . 1639) as per an aspect of an embodiment of the present invention. In these embodiments, one or more of clients (1610, 1611, . . . 1619) may have an LH*RE client 1610 configured to store a version of application data 1650 encrypted with an encryption key 1670 on remote servers (1631, 1632, 1633, . . . 1639). The remote servers (1631, 1632, 1633, . . . 1639) will likely be specialized servers configured to communicate with many client systems (1610, 1611 . . . 1619) and manage data buckets (1641, 1642, 1643, . . . 1649). The remote servers (1631, 1632, 1633, . . . 1639) may be geographically diverse. Some of the remote servers (1631, 1632, 1633, . . . 1639) may also be under the control of various organizations. In this way, the stored data may become harder for a third party to locate and retrieve all of the stored application data 1650 and key(s) 1670 from the data. Embodiments of the LH*RE client 1660 may be implemented as a computer readable storage medium containing a series of instructions that when executed by one or more processors on clients (1610, 1611, . . . 1619), causes the one or more processors to store application data 1650 on at least k+1 remote servers (1631, 1632, 1633, . . . 1639). In these embodiments, k is a freely set parameter of the system.

Figure 17:
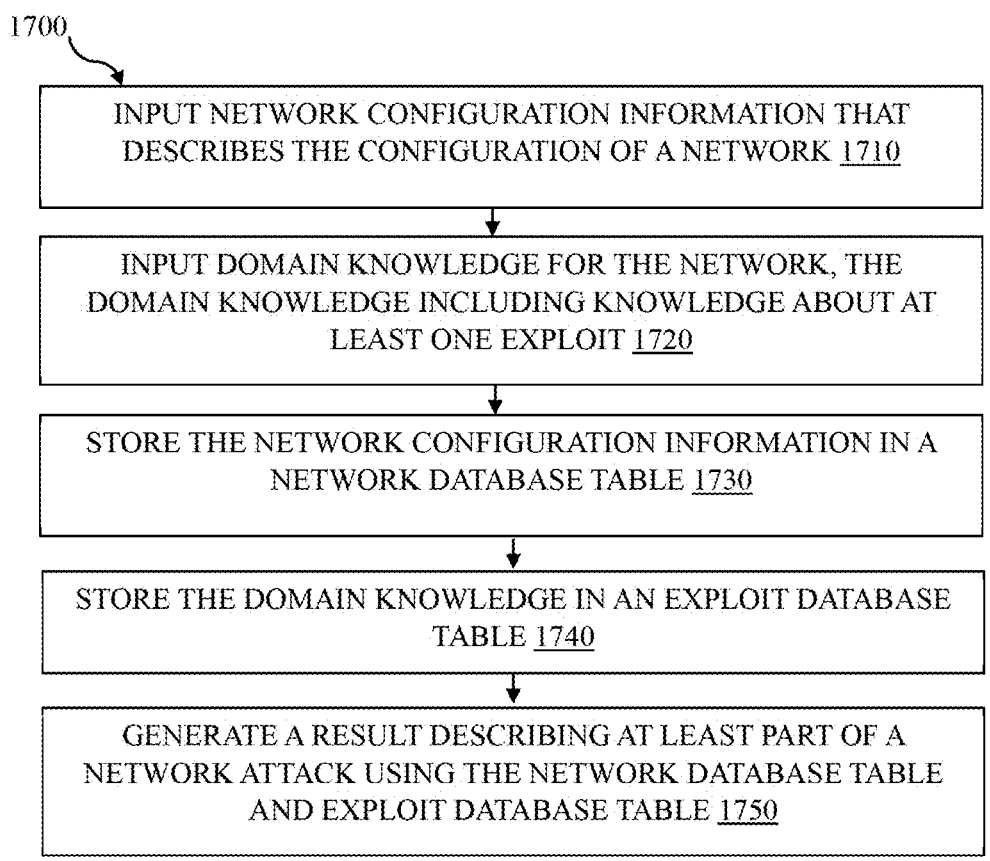
FIG. 17 is a flow diagram describing a method for determining at least part of a network attack according to an embodiment of the present invention.

Attack graphs depict ways in which an adversary exploits system vulnerabilities in a network such as a computer network. Attack graphs may be important in defending against well-orchestrated network intrusions. FIG. 17 is a flow diagram of an aspect of an embodiment where the network configuration information input module is preferably configured to input network configuration information that describes the configuration of a network in 1710. The domain knowledge input module is preferably configured to input domain knowledge for the network in 1720. Domain knowledge may include knowledge about various exploits in the network. The network configuration information storage module is preferably configured to store network configuration information in at least one network database table in 1730. Similarly, the domain knowledge storage module is preferably configured to store the domain knowledge in at least one exploit database table 1740. The result generation module is preferably configured to generate a result using the network database table and exploit database table in 1750. The result may be generated in many ways.

In an embodiment, an Intrusion Detection System (IDS) is deployed on the system. An IDS is software and/or hardware designed to detect unwanted attempts at accessing, manipulating, and/or disabling computer systems, mainly through a network, such as the Internet. An intrusion detection system is used to detect malicious behaviors that can compromise the security of networked computer systems. An IDS may include Sensor(s) that are deployed at strategic locations in the network, which monitor traffic at the sensor location and generate security events upon detection of malicious behaviors; A central engine that records events (e.g., in a database) logged by the sensors; and Console(s) to monitor events and control the sensors. In some IDS implementations, all three components are combined in a single device or appliance. In a true distributed system, numerous sensors are deployed at various points in the network, which communicate over secure channels to the central engine. Multiple consoles may then interact with the central engine. In network-based intrusion detection systems (NIDS), sensors are located at monitoring points in a network. Traditionally, sensors may be placed at network borders or in a network demilitarized zone (DMZ), with the assumption that attacks are launched from outside the network to be defended. The sensor monitors network traffic at its point of deployment and analyzes the traffic content for patterns of malicious behavior.

Embodiments of the present invention locate the placement of intrusion detection system (IDS) sensors and prioritize IDS alerts using attack graph analysis. One embodiment predicts multiple ways of penetrating a network to reach critical assets. The set of such paths through the network constitutes an attack graph, which may be aggregated according to underlying network regularities, reducing the complexity of analysis. By knowing the paths of vulnerability through our networks, one may reduce the impact of attacks. IDS sensors may be placed to cover the attack graph, using a minimal number of sensors. This should minimize the cost of sensors, including effort of deploying, configuring, and maintaining them, while maintaining complete coverage of potential attack paths. An embodiment addresses the sensor placement as an instance of the non-deterministic polynomial-time (NP) hard minimal set cover problem using an efficient greedy algorithm. Once sensors are deployed and alerts are raised, a predictive attack graph may be used to prioritize alerts based on attack graph distance to critical assets.

Figure 18:
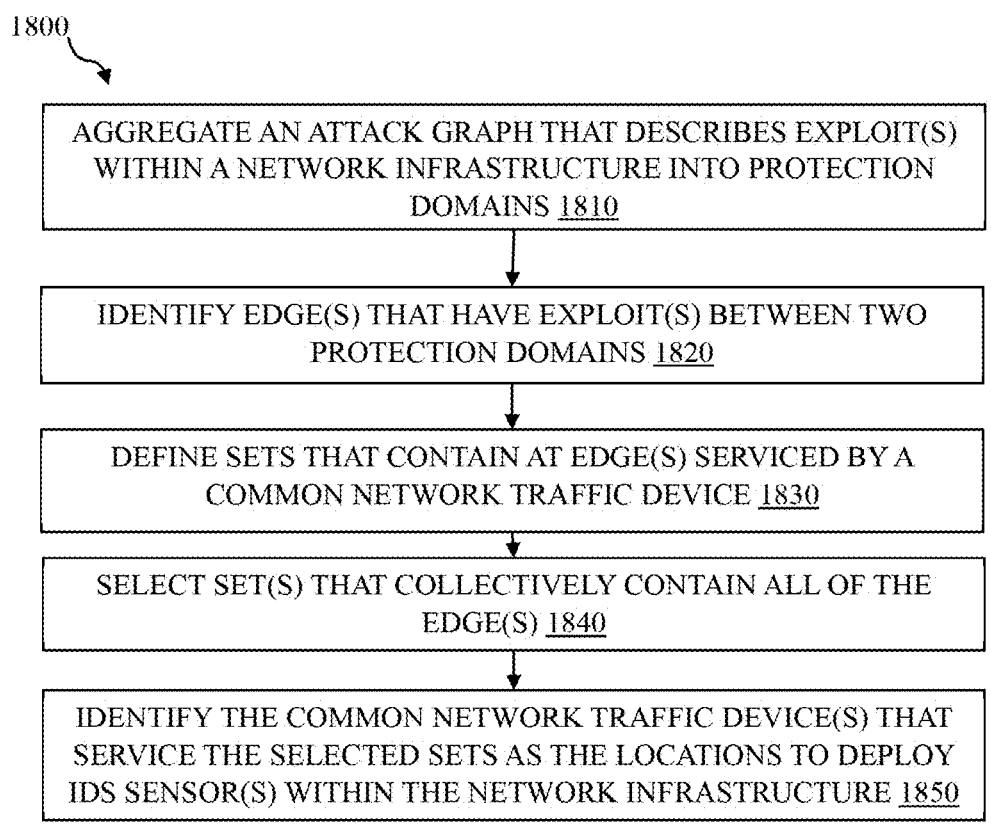
FIG. 18 depicts a flow diagram for a computer readable storage medium demonstrating instructions that cause the processor to perform a method for identifying locations to deploy intrusion detection system (IDS) Sensors within a network infrastructure, as per an aspect of an embodiment of the present invention.

An embodiment of the present invention, as exemplified in FIG. 18, is a computer readable storage medium that contains instructions that when executed by at least one processor, causes the processor(s) to perform a method 1800 for identifying locations to deploy IDS sensor(s) within a network infrastructure. The method 1800 for identifying locations to deploy IDS sensor(s) within a network may comprise aggregating an attack graph that describes exploit(s) within a network infrastructure into protection domains 1810. The attack graph may be configured to describe exploit(s) in at least a part of the network infrastructure. Further, the embodiment may include identifying edge(s) that have exploit(s) between two protection domains 1820, defining sets that contain edge(s) serviced by a common network traffic device 1830, selecting set(s) that collectively contain all of the edge(s) 1840, and identifying the common network traffic device(s) that service the selected sets as the locations to deploy IDS sensor(s) within the network infrastructure 1850.

In an embodiment of the present invention, the selecting set(s) that collectively contain all of the edge(s) 1840 may further include selecting set(s) that cover critical path(s) through the network infrastructure that lead to a critical asset. The set selection method 1840 may further include selecting set(s) that cover critical path(s) through the network infrastructure that starts at an assumed threat source. Further variations of this embodiment may allow the set selection method 1840 to include selecting a minimal number of sensors necessary to cover critical path(s) through the network infrastructure. The set selection method 1840 may also further include utilizing a greedy algorithm. The greedy algorithm favors large sets that contain edge(s) that are infrequently used. Frequency is the number of times an edge appears across all sets.

In an embodiment of the present invention, the method 1800 for identifying locations to deploy on IDS sensor(s) within a network may further include prioritizing alerts from IDS sensors deployed within the network infrastructure using at least one attack graph distance to at least one critical asset. Attack graph distance may be measured in multiple ways such as: 1) the number of edges that are traversed to reach critical assets; 2) the number of protection domains crossed; and 3) the number of network traffic devices.

In an aspect, a method is described herein. The method comprises: providing a therapy; and estimating an effect of the therapy through movement of eyes using an object; wherein the object comprises a mask that comprises a bio-monitoring system wherein the bio-monitoring system monitors a physiological state of a person. In an embodiment, the bio-monitoring system comprises an eye blink sensor and an eye movement sensor. In another embodiment, the bio-monitoring system comprises a web camera for pupil size measurements. In yet another embodiment, the bio-monitoring system further comprises a blood pressure measurement sensor, a pulse measurement sensor, an electrolyte levels measurement sensor, an oxygen level measurement sensor, a glucose level measurement sensor, and a body temperature measurement sensor. In an embodiment, the biomonitoring system is a modular auricular sensing system which can be used for monitoring the vital state. In yet another embodiment, the bio-monitoring system transmits a signal to a remote receiver.

The method of estimating the effect through movement of eyes comprises steps of:
a) Measuring an eye lid position and pupil size of an eye of a person at time T1;
b) Providing a psychedelic therapy to the person;
c) Monitoring a vital state of the person using a biomonitoring system;
d) Tracking eye lid position of the eye;
e) Tracking eye movement of the eye;
f) Monitoring a change in pupil size of the eye;
g) Comparing eye lid position and pupil size of the eye at time T2 with the eye lid position and pupil size of an eye of a person at time T1;
h) Analyzing the eye lid position, the pupil size, and eye movement of the eye to identify a change;
i) Correlating the change with the vital state and the duration of the therapy.

INCORPORATION BY REFERENCE

All references, including granted patents and patent application publications, referred to herein are incorporated herein by reference in their entirety.

U.S. Ser. No. 10/349,177 B2 titled "Wireless stereo sleep mask";
US20200261689A1 titled "Sleep enhancement system and wearable device for use therewith";
US20170252210A1 titled "Therapeutic eye mask system";
U.S. Ser. No. 10/974,020B2 titled "Systems and methods of mitigating negative effects of therapies with transcutaneous vibration";
US20210204852 titled "Methods and kits for diagnosing, assessing or quantitating drug use, drug abuse and narcosis";
USRE42471E1 titled "System and method for monitoring eye movement";
U.S. Pat. No. 8,870,740B2 titled "System and method for providing light therapy to a subject";
U.S. Pat. No. 6,193,740B1 titled "Eye pillows with adjustable strap";
U.S. Ser. No. 11/073,908B2 titled "Eye-tracking enabled wearable devices";
US20200410644A1 titled "Eye tracking method and apparatus";
U.S. Pat. No. 8,636,786B2 titled "Thermal compress system and methods of using the same";
U.S. Pat. No. 7,707,655B2 titled "Self warming mask";
US20200026087A1 titled "Augmented/Virtual Reality Near Eye Display with Edge Imaging Spectacle Lens";
US20170266035A1 titled "Wireless-controlled therapeutic warming eye wear device";
US20210015659A1 titled "Therapeutic eye mask";
US20050070977A1 titled "Light and magnetic emitting mask";
U.S. Ser. No. 10/905,846B2 titled "Phototherapy sleep mask";
U.S. Pat. No. 9,203,861B2 titled "Methods and systems for determining hardening strategies";
U.S. Pat. No. 9,436,822B2 titled "Virtual browsing environment";
U.S. Ser. No. 10/956,184B2 titled "Malware detector";
U.S. Pat. No. 9,846,588B2 titled "on demand disposable virtual work system";
U.S. Pat. No. 8,082,452B2 titled "Protecting sensitive data associations";
US20100054481A1 titled "Scalable distributed data structure with recoverable encryption";
U.S. Pat. No. 8,566,269B2 titled "Interactive analysis of attack graphs using relational queries";
US20100058456A1 titled "IDS sensor placement using attack graphs".

What is claimed is:

1. A system comprising:
an object comprising a mask comprising a first portion to cover an eye of a person, the first portion comprising a first layer and a second layer adjacent to the first layer, and an eye pocket;
an attachable device; and
a bio-monitoring system comprising a neurological sensor and an acoustic sensor; and
wherein the first layer and the second layer form a pouch;
a control unit comprising a cyber security module;
wherein the system is configured to provide a combination therapy comprising at least two therapies, wherein a first therapy comprises a psychedelic drug therapy;
wherein a second therapy comprises at least one of an aromatherapy, a sound therapy, an acupressure therapy, a massage therapy, a temperature therapy, a magnetic therapy, and a visual based stress relief therapy;
wherein the bio-monitoring system monitors a physiological state of the person in response to the psychedelic drug therapy;
wherein the physiological state comprises a state of body of the person, bodily functions, mental state, and emotional state;
wherein the combination therapy is automatically adjusted based on the physiological state; and
wherein system is configured to adjust the combination therapy by at least one of changing the second therapy, modifying the first therapy, modifying the second therapy, stopping the first therapy, and stopping the second therapy.

2. The system of claim 1, wherein the eye pocket is deep molded and concave.

3. The system of claim 1, wherein the eye pocket further comprises a 3D contoured cup configured to apply stress-relieving pressure around the eye and wherein the 3D contoured cup is configured to form a space between the eye and the eye pocket.

4. The system of claim 3, wherein the space is configured to hold at least one of a patch comprising a nutrient material, an eye pillow, and a gel pad.

5. The system of claim 1, wherein the attachable device comprises an audio device, a microphone, an aroma infusion device, a visual display, a heating device, a cooling device, an eye massage device, and a light emitting device.

6. The system of claim 1, wherein the bio-monitoring system further comprises an eye movement sensor.

7. The system of claim 1, wherein a second portion of the mask comprises an adjustable strap.

8. The system of claim 1, wherein the pouch is filled with a fill material.

9. The system of claim 8, wherein the fill material comprises an aromatic substance.

10. The system of claim 1, wherein the control unit further comprises an input module, a processor, a communication module, a database, a user interface, a universal serial bus, a controller, a display, and a power module.

11. The system of claim 10, wherein the system can communicate data to a server via the communication module.

12. The system of claim 1, wherein the bio-monitoring system further comprises a web camera for pupil size measurements.

13. The system of claim 1, wherein the bio-monitoring system further comprises a blood pressure measurement sensor.

14. The system of claim 1, wherein the first layer and the second layer are made from one of a silk fabric, a cotton fabric, a wool fabric, a nylon fabric, a velvet fabric, a polyester fabric, a synthetic fabric, a suitable fabric, and combination thereof.

15. The system of claim 1, wherein the bio-monitoring system is one of an inbuilt and detachable.

16. The system of claim 1, wherein the attachable device and the bio-monitoring system are configured to be remotely controlled.

* * * * *